United States Patent [19]

Haslanger et al.

[11] Patent Number: 5,061,710

[45] Date of Patent: Oct. 29, 1991

[54] MERCAPTO-ACYLAMINO ACID ANTIHYPERTENSIVES

[75] Inventors: Martin F. Haslanger, Ridgewood; Bernard R. Neustadt, West Orange; Elizabeth M. Smith, Verona, all of N.J.

[73] Assignee: Schering Corporation, Kenilworth, N.J.

[21] Appl. No.: 133,669

[22] Filed: Dec. 16, 1987

Related U.S. Application Data

[63] Continuation-in-part of Ser. No. 32,153, Mar. 27, 1987, Pat. No. 4,801,609.

[30] Foreign Application Priority Data

Jun. 17, 1987 [EP]  European Pat. Off. ........ 87108730-0

[51] Int. Cl.$^5$ ............................................ A61K 307/07
[52] U.S. Cl. ........................................ 514/266; 514/13
[58] Field of Search .............. 514/522, 533, 538, 539, 514/540, 542, 546, 547, 548, 549, 550, 551, 552, 558, 559, 560, 561, 562, 616, 618, 211, 212, 218, 324, 326, 252, 233.5, 320, 315, 255, 238.2, 228.8, 415, 427, 397, 374, 419, 400, 399, 513, 266, 265, 354, 356, 337, 469, 471, 448, 433, 444, 422, 428, 452, 459, 467, 12, 13; 530/324, 325, 326; 206/568

[56] References Cited

U.S. PATENT DOCUMENTS

| | | |
|---|---|---|
| 4,053,651 | 10/1977 | Ondetti et al. ........................ 514/522 |
| 4,105,776 | 8/1978 | Ondetti et al. ........................ 514/12 |
| 4,228,077 | 10/1980 | Ondetti et al. ........................ 514/12 |
| 4,256,761 | 3/1981 | Suh et al. ........................ 514/12 |
| 4,329,495 | 5/1982 | Bindra ........................ 514/522 |
| 4,344,949 | 8/1982 | Hoefle et al. ........................ 514/12 |
| 4,350,704 | 9/1982 | Hoefle et al. ........................ 514/12 |
| 4,374,829 | 2/1983 | Harris et al. ........................ 514/12 |
| 4,374,847 | 2/1983 | Gruenfeld ........................ 514/12 |
| 4,401,677 | 4/1983 | Greenberg et al. ........................ 514/522 |
| 4,410,520 | 10/1983 | Watthey ........................ 514/12 |
| 4,462,943 | 7/1984 | Petrillo et al. ........................ 514/12 |
| 4,468,519 | 8/1984 | Krapcho ........................ 514/12 |
| 4,470,972 | 9/1984 | Gold et al. ........................ 514/12 |
| 4,470,973 | 9/1984 | Natarajan et al. ........................ 514/12 |
| 4,500,467 | 2/1985 | Kubinyi et al. ........................ 514/522 |
| 4,508,729 | 4/1985 | Vincent et al. ........................ 514/12 |
| 4,512,924 | 4/1985 | Attwood et al. ........................ 514/12 |
| 4,513,009 | 4/1985 | Roques et al. ........................ 514/522 |
| 4,555,506 | 11/1985 | Karanewsky et al. ........................ 514/12 |
| 4,740,499 | 4/1988 | Olins ........................ 514/522 |

FOREIGN PATENT DOCUMENTS

| | | |
|---|---|---|
| 0038046 | 10/1981 | European Pat. Off. ........... 514/522 |
| 46953 | 3/1982 | European Pat. Off. ........... 514/12 |
| 50800 | 5/1982 | European Pat. Off. ........... 514/12 |
| 79022 | 5/1983 | European Pat. Off. ........... 514/12 |
| 79522 | 6/1983 | European Pat. Off. ........... 514/12 |
| 136883 | 4/1985 | European Pat. Off. ........... 514/522 |
| 637374 | 7/1983 | Switzerland ........................ 514/522 |
| 2095682 | 10/1982 | United Kingdom ................. 514/12 |

OTHER PUBLICATIONS

Needleman et al., *N. Eng. J. Med.*, 314, 13 (1986), pp. 828–834.
Cantin et al., *Scientific American*, 254 (1986), pp. 76–81.
Wyvratt et al., *Med. Res. Rev.*, 5, No. 4 (1985), pp. 483–531.
Brock et al., *Hypertension*, Supp. II, 4, No. 3 (1982), pp. II43–II48.

*Primary Examiner*—Mary C. Lee
*Assistant Examiner*—Robert C. Whittenbaugh
*Attorney, Agent, or Firm*—Anita W. Magatti; James Nelson

[57] ABSTRACT

Novel mercapto-acylamino acids useful in the treatment of hypertension and combinations of mercapto-acylamino acids and atrial natriuretic factors or angiotensin converting enzyme inhibitors useful for treating hypertension are disclosed.

4 Claims, No Drawings

MERCAPTO-ACYLAMINO ACID ANTIHYPERTENSIVES

This application is a continuation-in-part of Ser. No. 032,153, filed Mar. 27, 1987, now U.S. Pat. No. 4,801,609.

SUMMARY OF THE INVENTION

The present invention relates to mercapto-acylamino acids useful in the treatment of hypertension and congestive heart failure.

The invention also relates to the treatment of hypertension and congestive heart failure with a combination of a mercapto-acylamino acid and an atrial natriuretic factor (ANF) and with a combination of a mercapto-acylamino acid and an angiotensin converting enzyme (ACE) inhibitor.

Other aspects of the invention relate to pharmaceutical compositions comprising a mercapto-acylamino acid of this invention, alone or in combination with an ANF or an ACE inhibitor, and to methods of treatment of hypertension and congestive heart failure comprising administering a mercapto-acylamino acid of this invention, alone or in combination with an ANF or an ACE inhibitor to a mammal in need of such treatment.

BACKGROUND OF THE INVENTION

Human hypertension represents a disease of multiple etiologies. Included among these is a sodium and volume dependent low renin form of hypertension. Drugs that act to control one aspect of hypertension will not necessarily be effective in controlling another.

A variety of mercapto-acylamino acids are known as enkephalinase inhibitors useful as analgesics and in the treatment of hypertension.

U.S. Pat. No. 4,513,009 to Roques et al discloses, inter alia, compounds of the formula.

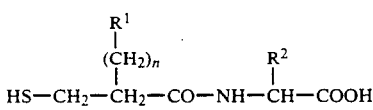

wherein n is 0 to 1; $R^1$ includes substituted alkyl, optionally substituted phenyl, cyclohexyl and thienyl; and $R^2$ includes hydrogen optionally substituted alkyl, optionally substituted benzyl, phenyl, phenoxyalkyl and optionally substituted mercaptoalkyl. The compounds are disclosed as principally having enkephalinase activity, but also are said to be antihypertensives.

U.S. Pat. No. 4,401,677 to Greenberg et al and EPA 38,046 to Wilkinson disclose compounds of a scope similar to Roques et al, the former disclosing analgesic activity and the latter disclosing a greater specificity for enkephalinase than ACE. U.S. Pat. No. 4,053,651 to Ondetti et al discloses the use of similar compounds in the treatment of renin-angiotensin related hypertension.

It has recently been discovered that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homeostasis", N. Engl. J. Med., 314, 13 (1986) pp. 828–834, and M. Cantin et al. in "The Heart as an Endocrine Gland", Scientific American, 254 (1986) pg. 76–81.

A class of drugs known to be effective in treating some types of hypertension is ACE inhibitors, which compounds are useful in blocking the rise in blood pressure caused by increases in vascular resistance and fluid volume due to the formation of angiotensin II from angiotensin I. For a review of ACE inhibitors, see M. Wyvratt and A. Patchett, "Recent Developments in the Design of Angiotensin Converting Enzyme Inhibitors" in Med. Res. Rev. Vol. 5, No. 4 (1985) pp. 483–531.

DETAILED DESCRIPTION

Novel antihypertensive compounds of the present invention are represented by the following formulae:

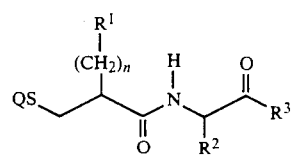

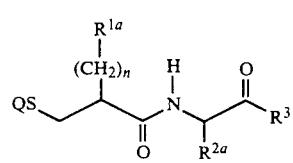

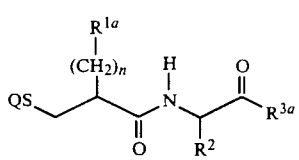

wherein $R^1$ is phenyl substituted by one or more substituents independently selected from alkyl, alkoxy, cycloalkyl, cyano and aminomethyl, $Y-C_6H_4S-$, $Y-C_6H_4O-$,

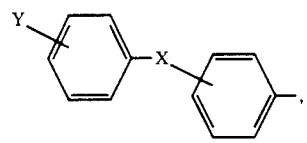

α-naphthyl, β-naphthyl, furyl, benzofuryl, benzothienyl, $H_2N(CH_2)_m-$, diphenylmethyl

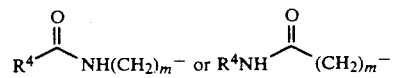

$R^2$ is alkyl, alkyl—$S(O)_{0-2}(CH_2)_q-$, $R^{14}(CH_2)_kS(O)_{0-2}(CH_2)_q-$, alkyl—$O(CH_2)_q-$, $R^5(CH_2)_k-O(CH_2)_q-$, $R^5(CH_2)_q-$, $H_2N(CH_2)_q-$, cycloalkyl$(CH_2)_k-$, $R^{13}CONH(CH_2)_q-$, $R^{13}NHCO(CH_2)_q-$ or $R^6O-CO(CH_2)_q-$;

$R^3$ is $-OR^7$,

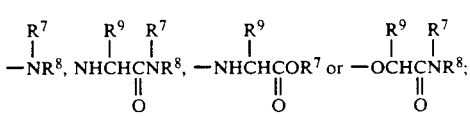

R[4] and R[13] are independently hydrogen, alkyl or Y[1]—C$_6$H$_4$—;

R[5] is Y[2]—C$_6$H$_4$—, Y[2]—C$_6$H$_4$S—, Y[2]—C$_6$H$_4$O—, α-naphthyl, β-naphthyl, furyl, thienyl, benzofuryl, benzothienyl, indolyl or

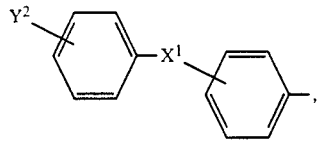

provided that when R[5] is Y[2]—C$_6$H$_4$S— or Y[2]—C$_6$H$_4$O—, k is 2 or 3;

R[14] is R[5], mono-unsaturated lower alkyl, hydroxy, alkoxy or alkylthio, provided that when R[14] is hydroxy or alkoxy, k is 2 or 3 and when R[14] is mono-unsaturated alkykl or alkylthio, k is 1, 2 or 3;

R[6], R[7] and R[8] are independently H, alkyl, hydroxyalkyl, dihydroxyalkyl, alkoxyalkyl, dialkoxyalkyl, alkoxyalkoxyalkyl, haloalkyl, (haloalkoxy)alkyl, aminoalkyl, alkylaminoalkyl, dialkylaminoalkyl, arylalkyl or alkyl substituted with a 5-6 membered saturated ring comprising 1-2 oxygen atoms as ring members wherein the ring carbon atoms may be substituted with 0-2 alkyl substituents, or R[7] and R[8] together with the nitrogen to which they are attached complete a 5-7 membered ring, wherein one of the 4-6 ring members comprising R[7] and R[8] may be a nitrogen atom, an alkyl-substituted nitrogen atom or an oxygen atom, and wherein the ring may be substituted on the ring carbon atoms with substituents chosen from alkyl and hydroxy groups;

R[9] is hydrogen, alkyl, carboxyalkyl, mercaptoalkyl, alkylthioalkyl, aminoalkyl, hydroxyalkyl, phenylalkyl, hydroxyphenylalkyl, guanidinoalkyl, imidazolylalkyl, indolylalkyl or carbamoylalkyl;

n is 0-2;

m and k are independently 0-3;

q is 1-4;

X and X[1] are independently a bond, —O—, —S—, or —CH$_2$—;

Q is hydrogen or R[10]CO—;

R[10] is alkyl, hydroxyalkyl, alkoxyalkyl, dialkylaminoalkyl, Y[3]—C$_6$H$_4$-alkyl, alkoxy, Y[3]—C$_6$H$_4$—, naphthyl, furyl, thienyl or pyridyl;

Y, Y[1], Y[2] and Y[3] independently represent one or more substituents selected from H, alkyl, cycloalkyl, alkoxy, OH, F, Cl, Br, CN, —CH$_2$NH$_2$, —CO$_2$H, —CO$_2$alkyl, —CONH$_2$ and phenyl;

R[1a] is Y—C$_6$H$_4$—, Y—C$_6$H$_4$S—, Y—C$_6$H$_4$O—,

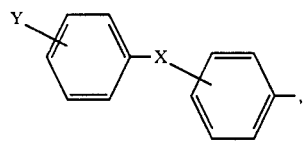

α-naphthyl, β-naphthyl, furyl, thienyl, benzofuryl, benzothienyl, H$_2$N(CH$_2$)$_m$—, diphenylmethyl,

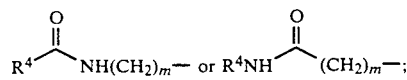

R[2a] is R[14a](CH$_2$)$_k$S(O)$_{0-2}$(CH$_2$)$_q$—, R[5a](CH$_2$)$_k$—O(CH$_2$)$_q$—, R[5a](CH$_2$)$_q$—, or cycloalkyl-(CH$_2$)$_k$, and when R[3] is —NR[7]R[8],

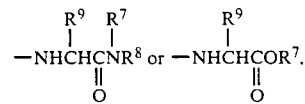

R[2a] may also be indolyl-(CH$_2$)$_q$—, R[13]CONH(CH$_2$)$_q$—, R[13]NHCO(CH$_2$)$_q$— or R[6]OCO(CH$_2$)$_q$—;

R[3a] is

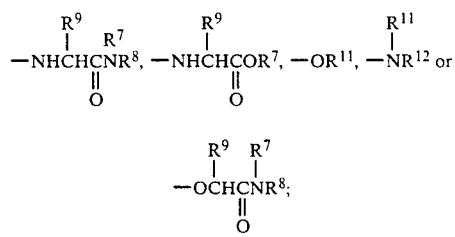

R[11] is hydroxyalkyl, dihydroxyalkyl, alkoxyalkyl, dialkoxyalkyl, alkoxyalkoxyalkyl, haloalkyl, (haloalkoxy)alkyl, alkyl substituted with a 5-6 membered saturated ring comprising 1-2 oxygen atoms as ring members wherein the ring carbon atoms may be substituted with 0-2 alkyl substituents, or substituted phenylalkyl wherein the phenyl group is substituted by one or more groups selected from alkyl, alkoxy, cycloalkyl and cyano; R[12] is H or selected from the same group as R[11]; or R[11] and R[12] together with the nitrogen to which they are attached complete a 5-7 membered ring wherein one of the 4-6 ring members comprising R[11] and R[12] may be a nitrogen atom, an alkyl-substituted nitrogen atom or an oxygen atom, and wherein the ring may be substituted on the ring carbon atoms with substituents chosen from alkyl and hydroxy groups;

R[5a] is Y[2]—C$_6$H$_4$ provided Y[2] is not H or OH, Y[2]—C$_6$H$_4$S—, Y[2]—benzofuryl, benzothienyl or

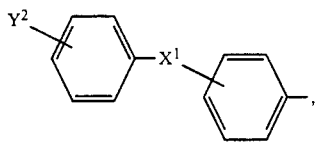

provided that when R[5a] is Y[2]—C$_6$H$_4$—S— or Y[2]—C$_6$H$_4$O—, k is 2 or 3;

R[14a] is R[5a], mono-unsaturated alkyl, hydroxy, alkoxy or alkylthio, provided that when R[14a] is hydroxy or alkoxy, k is 2 or 3 and when R[14a] is mono-unsaturated alkyl or alkylthio, k is 1, 2 or 3;

and the pharmaceutically acceptable addition salt thereof.

As used herein the term "alkyl" means straight or branched alkyl chains of 1 to 6 carbon atoms, and "alkoxy" similarly refers to alkoxy groups having 1 to 6 carbon atoms. "Cycloalkyl" means cyclic alkyl groups of 3-6 carbon atoms.

"Aryl" means mono-cyclic or fused ring bicyclic aromatic groups having 5 to 10 ring members wherein 0-2 ring members may independently be nitrogen, oxygen or sulfur and wherein the ring members may be substituted by one to three substituents chosen from group Y defined above. Examples of aryl groups are phenyl, α-naphthyl, β-naphthyl, furyl, thienyl, benzofuryl, benzothienyl, indolyl and pyridyl.

"Halo" refers to fluorine, chlorine, bromine or iodine radicals. The term "poly", when used to describe substitution in a phenyl, alkylphenyl or alkoxyphenyl group, means 2 to 5 substituents.

Groups $R^3$ and $R^{3a}$ comprising the partial structure

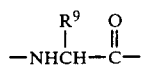

are derived from amino acids of formula

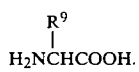

Examples of such amino acids are alanine, arginine, asparagine, aspartic acid, cysteine, glutamine, glutamic acid, glycine, histidine, isoleucine, leucine, lysine, methionine, phenylalanine, serine, threonine, tryptophan, tyrosine and valine.

Preferred embodiments of compounds of formula I are compounds wherein $R^2$ is alkyl, alkyl—S(O)$_{0-2}$(CH$_2$)$_q$—, $R^{14}$(CH$_2$)$_k$S(O)$_{0-2}$(CH$_2$)$_q$— or $R^5$(CH$_2$)$_q$—, wherein $R^{14}$, $R^5$, q and k are as defined above. Also preferred are compounds of formula I wherein $R^1$ is naphthyl, furyl, benzofuryl, benzothienyl, diphenylmethyl, aminoalkyl, Y—C$_6$H$_4$—X—C$_6$H$_4$—, $R^4$CONH(CH$_2$)$_m$— or $R^4$NHCO(CH$_2$)$_m$—, wherein Y, X, $R^4$ and m are as defined above. A third group of preferred compounds in that wherein $R^1$ is substituted phenyl. Still another group of preferred compounds of formula I is that wherein $R^3$ is —OR$^7$ or —NR$^7$R$^8$, wherein $R^7$ and $R^8$ are as defined above.

Preferred compounds of formula II are those wherein $R^{2a}$ is $R^{13a}$(CH$_2$)$_k$S(O)$_{0-2}$(CH$_2$)$_q$— wherein $R^{14a}$, q and k are as defined above. Also preferred are compounds of the formula II wherein $R^{1a}$ is naphthyl, furyl, thienyl, benzofuryl, benzothienyl, diphenylmethyl, aminoalkyl, Y—C$_6$H$_4$—X—C$_6$H$_4$—, $R^4$CONH(CH$_2$)$_m$— or $R^4$NHCO(CH$_2$)$_m$— wherein Y, X, $R^4$ and m are as defined above. A third group of preferred compounds is that wherein $R^{1a}$ is Y—C$_6$H$_4$. Still another group of preferred compounds of formula II is that wherein $R^3$ is —OR$^7$ or —NR$^7$R$^8$, wherein $R^7$ and $R^8$ are as defined above.

Preferred compounds of formula III are those wherein $R^{3a}$ is —OR$^{11}$, —NHCH$_2$CONH$_2$, arylalkoxy or arylalkylamino. Also preferred are compounds wherein $R^{1a}$ is phenyl or substituted phenyl. Also preferred are compounds wherein $R^2$ is alkyl—S(O)$_{0-2}$(CH$_2$)$_q$—, especially CH$_3$SCH$_2$CH$_2$— or CH$_3$SOCH$_2$CH$_2$.

Preferred —OR$^7$ and —OR$^{11}$ groups are those wherein the $R^7$ and $R^{11}$ groups are selected from (haloalkoxy)alkyl, alkoxyalkyl, alkoxyalkoxyalkyl, dihydroxyalkyl and 2,2-dimethyl-1,3-dioxolan-4-yl-methyl.

Preferred compounds of formulae I–III are those wherein Q is hydrogen or $R^{10}$CO— wherein $R^{10}$ is alkyl, especially methyl, or phenyl.

Especially preferred are compounds of formula III wherein $R^{1a}$ is optionally substituted phenyl, n is 1, $R^2$ is CH$_3$SCH$_2$CH$_2$— or CH$_3$SOCH$_2$CH$_2$—, $R^{3a}$ is —OR$^{11}$ wherein $R^{11}$ is alkoxyalkyl, dihydroxyalkyl, alkoxyalkoxyalkyl, (haloalkoxy)alkyl or 2,2-dimethyl-1,3-dioxolan-4-yl-methyl, and Q is hydrogen, acetyl or benzoyl.

Preferred compounds include the (R,S) and (S,S) isomers and the corresponding free acids (i.e., $R^{3a}$ is OH) of the following:

N-(2-benzoylthiomethyl-3-phenylpropionyl)-S-methionine 2-(2-chloroethoxy)ethyl ester;

N-(2-benzoylthiomethyl-3-phenylpropionyl)-S-methionine 2-(ethoxy)ethyl ester;

N-(2-benzoylthiomethyl-3-phenylpropionyl)-S-methionine 2,2-dimethyl-1,3-dioxolan-4-methyl ester;

N-(2-benzoylthiomethyl-3-phenylpropionyl)-S-methionine 2-(2-methoxyethoxy)ethyl ester;

(2-acetylthiomethyl-3-phenylpropionyl)-S-methionine 2-(2-chloroethoxy)ethyl ester;

N-(2-acetylthiomethyl-3-(4-methylphenyl)propionyl)-S-methionine 2-(2-chloroethoxy)ethyl ester;

N-(2-acetylthiomethyl-3-(2-methylphenyl)propionyl)-S-methionine 2-(2-chloroethoxy)ethyl ester;

N-(2-benzoylthiomethyl-3-phenylpropionyl)-S-methionine 2,3-dihydroxypropyl ester; and N-(2-benzoylthiomethyl-3-phenylpropionyl)-S-methionine sulfoxide 2-(2-chloroethoxy)ethyl ester.

Compounds of this invention may, depending on the nature of functional groups, form addition salts with various inorganic and organic acids and bases. Such salts include salts prepared with organic and inorganic acids, e.g. HCl, HBr, H$_2$SO$_4$, H$_3$PO$_4$, methanesulfonic acid, toluenesulfonic acid, maleic acid, furmaric acid and camphorsulfonic acid. Salts prepared with bases include ammonium salts, alkali metal salts, e.g. sodium and potassium salts, and alkaline earth salts, e.g. calcium and magnesium salts.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of formulae I–III have two or more asymmetrical carbon atoms and therefore include various stereoisomers. All stereoisomers are included within the scope of the present invention.

Compounds of the present invention may be prepared by using coupling reactions well known in the peptide art to join a 3-acetylthio-2-(substituted)-propionic acid of formula 1 with an amino acid ester of formula 2. The following reaction Scheme 1 is an example:

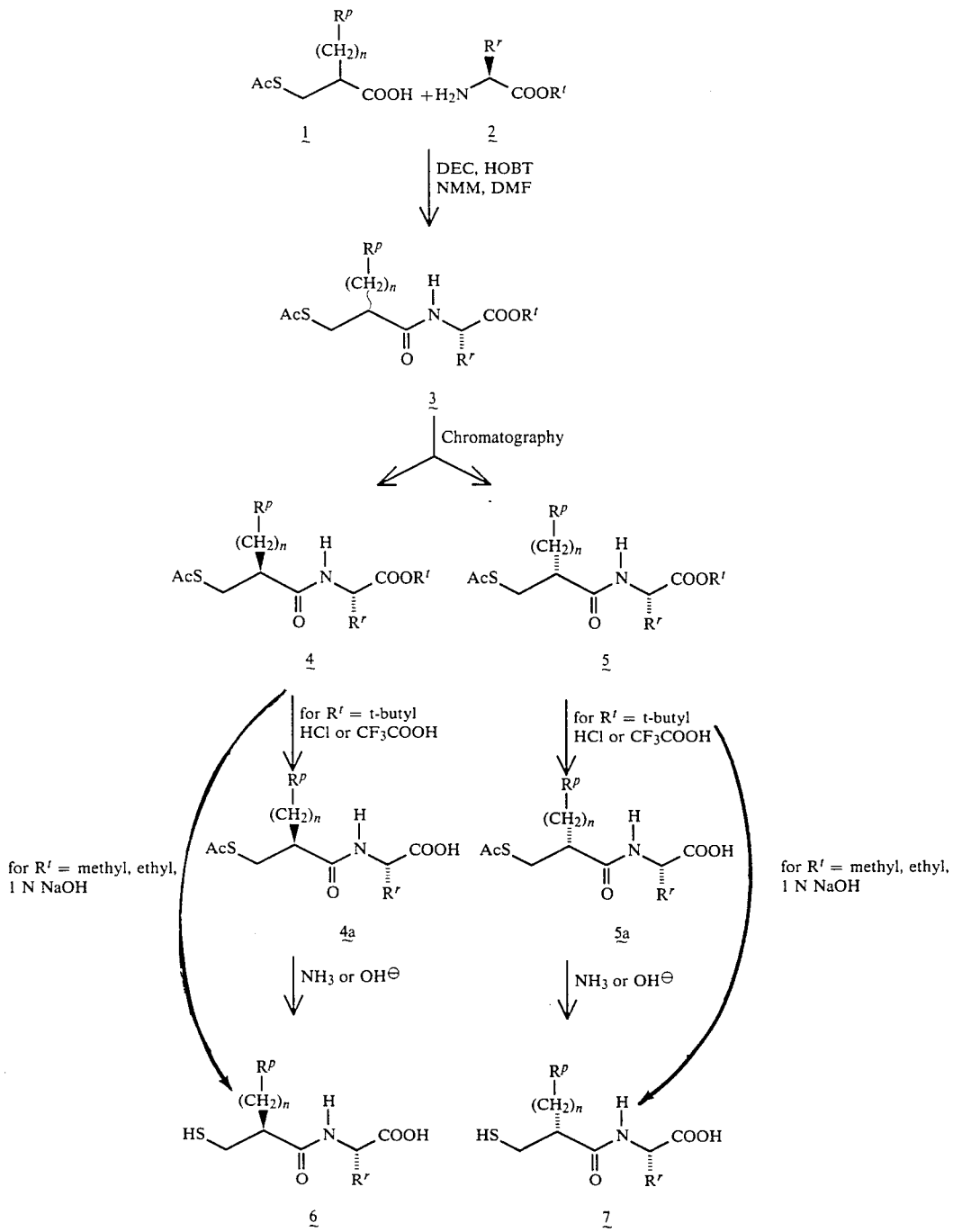

In the above scheme, $R^p=R^1$ and $R^{1a}$; $R^r=R^2$ and $R^{2a}$; $R^t$ is methyl, ethyl, t-butyl or aralkyl (e.g. benzyl); Ac is acetyl; n is 0–2; DEC is 1-(3-dimethylaminopropyl)-3-ethylcarbodiimide hydrochloride; HOBT is 1-hydroxybenzotriazole hydrate; NMM is N-methylmorpholine; and DMF is dimethylformamide.

As Scheme 1 shows, an amino acid ester of formula 2 and a 3-acetylthio propionic acid of formula 1 are reacted at room temperature in an inert solvent such as DMF in the presence of coupling agents such as DEC and HOBT in the presence of a base such as NMM. The resultant isomers are separated by chromatography and the isomers are deprotected at the acid and mercapto positions.

Alternatively, a propionic acid of formula 1 may be reacted with thionyl chloride to prepare the corresponding propionyl chloride, which may then be reacted with an amino acid ester of formula 2 or with the corresponding free acid 2a in an inert solvent such as acetonitrile in the presence of a base such as triethylamine to give isomers of formula 3, which may be separated as in Scheme 1. The following Scheme 2 is an example:

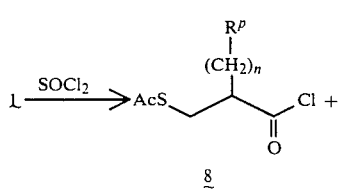

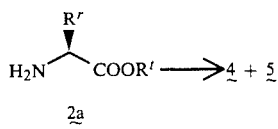

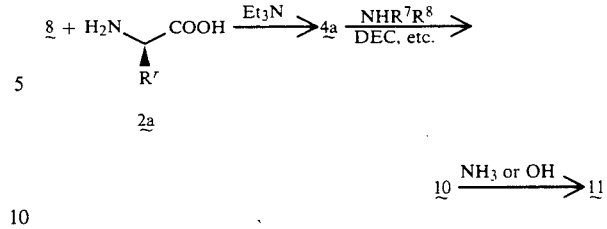

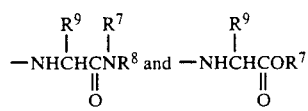

wherein n, Ac, $R^p$, $R^r$ and $R^t$ are as defined above, and wherein $R^t$ may also be hydrogen.

Other $R^3$ and $R^{3a}$ esters of compounds of formulae I–III are prepared by standard esterification techniques, for example N-(t-butoxycarbonyl)-S-methionine is reacted with 2-(2-chloroethoxy)ethanol in the presence of a base such as 4-dimethylaminopyridine, the amino function is deprotected and the resultant amino acid ester is reacted with a compound of formula 1 in a manner similar to that described in Scheme 2. In another example, N-(t-butoxycarbonyl)-S-methionine is reacted with N,N-diethylbromoacetamide and a reagent such as cesium carbonate, the resultant ester is deprotected at the amino function and a reaction similar to that described in Scheme 2 is carried out.

Compounds of formulae I–III wherein $R^3$ or $R^{3a}$ is $-NR^7R^8$ are prepared by coupling reactions as described above in Schemes 1 and 2 by replacing the amino acid ester 2 with an amide or substituted amide as shown in Scheme 3:

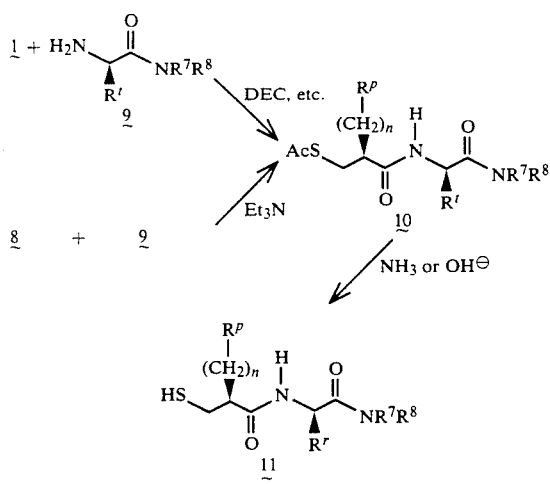

Alternatively, compounds of formulae I–III wherein $R^3$ or $R^{3a}$ is $-NR^7R^8$ may be prepared by coupling a propionyl chloride of formula 8 with an amino acid of formula 2a in the presence of a base and then coupling the desired $-NR^7R^8$ group to the carboxylic group using a typical peptide-coupling reaction. Scheme 4 shows an example of such a procedure:

A third method for preparing compounds of formulae I–III wherein $R^3$ or $R^{3a}$ is $-NR^7R^8$ comprises reacting a propionic acid of formula 1 with an amino acid t-butyl ester of formula 2, removing the t-butyl ester and coupling the $-NR^7R^8$ group to the carboxylic acid group as above.

Compounds wherein $R^3$ and $R^{3a}$ are $$\begin{matrix} R^9 & R^7 & & R^9 \\ | & | & & | \\ -NHCHCNR^8 & \text{and} & -NHCHCOR^7 \\ \parallel & & & \parallel \\ O & & & O \end{matrix}$$

are prepared analogously to those wherein $R^3$ and $R^{3a}$ are $-NR^7R^8$.

Compounds wherein Q is $R^{10}CO-$ may be prepared by known methods, for example by adding a mercaptoacid of formula $R^{10}$ COSH to an acrylic acid to obtain a thiosubstituted propionic acid analogous to compounds of formula 1. Alternatively, an amide of formulae I–III wherein Q is hydrogen $-SH$ may be reacted with a compound of formulae $R^{10}COCl$ is the presence of a base to obtain the desired sulfur substituted derivative.

Compounds wherein $R^2$ or $R^{2a}$ is, e.g. alkyl—S(O)-$_{1-2}(CH_2)_q-$ or $R^{14}(CH_2)_k-S(O)_{1-2}(CH_2)_q-$, are prepared by oxidizing with hydrogen peroxide the corresponding alkylthioalkyl compounds of formulae I–III (e.g. those wherein $R^2$ or $R^{2a}$ is, e.g. alkyl—S—(CH$_2$-)$_q-$ or $R^{14}(CH_2)_k-S-(CH_2)_q-$).

Starting materials of formulae 1 and 2 are known in the art or may be prepared by methods well known to those skilled in the art. Examples of typical preparations of starting materials and specific examples of compounds of formulae I–III are provided at the end of the specification.

A second aspect of the invention is the administration of a combination of an ANF and a compound of the following formula IV

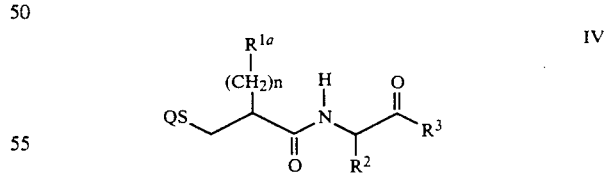

wherein n, $R^{1a}$, $R^2$, $R^3$ and Q are as defined above, for the treatment of hypertension. Compounds of formula IV have chiral centers and form addition salts as described above for compounds of formulae I–III, and may be prepared by similar methods.

As indicated by Needleman et al., a number of ANF have been isolated so far, all having the same core sequence of 17 amino acids within a cysteine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain isoleucine. Various synthetic analogs of naturally occurring ANFs also have been found to have comparable biological activity. Examples of ANFs contemplated for use in this invention are α human AP 21 (atriopeptin I), α human AP 28, α human AP 23 (atriopeptin II or APII), α human AP 24, α human AP 25, α human AP 26, α human AP 33, and the corresponding rat sequence of each of the above wherein Met 12 is Ile. See Table 1 for a comparison of the peptides.

TABLE 1

HUMAN PEPTIDE

| AP 21 | AP 23 | AP 24 | AP 25 | AP 26 | AP 28 | AP 33 |
|-------|-------|-------|-------|-------|-------|-------|
|       |       |       |       |       |       | Leu   |
|       |       |       |       |       |       | Ala   |
|       |       |       |       |       |       | Gly   |
|       |       |       |       |       |       | Pro   |
|       |       |       |       |       |       | Arg   |
|       |       |       |       |       | Ser   | Ser   |
|       |       |       |       |       |       | Leu   |
|       |       |       |       | Arg   | Arg   | Arg   |
|       |       |       | Arg   |       |       | Arg   |
| Ser   | Ser   | Ser   |       |       |       | Ser   |
|       |       |       |       |       |       | Ser   |
|       |       |       |       |       |       | Cys—S—┐ |
|       |       |       |       |       |       | Phe   |
|       |       |       |       |       |       | Gly   |
|       |       |       |       |       |       | Gly   |
|       |       |       |       |       |       | Arg   |
|       |       |       |       |       |       | Met*  |
|       |       |       |       |       |       | Asp   |
|       |       |       |       |       |       | Arg   |
|       |       |       |       |       |       | Ile   |
|       |       |       |       |       |       | Gly   |
|       |       |       |       |       |       | Ala   |
|       |       |       |       |       |       | Gln   |
|       |       |       |       |       |       | Ser   |
|       |       |       |       |       |       | Gly   |
|       |       |       |       |       |       | Leu   |
|       |       |       |       |       |       | Gly   |
|       |       |       |       |       |       | Cys—S—┘ |
|       |       |       |       |       |       | Asn   |
| Ser   |       |       |       |       |       | Ser   |
|       |       |       |       |       |       | Phe   |
|       | Arg   |       |       |       |       | Arg   |
|       | Tyr   | Tyr   | Tyr   | Tyr   | Tyr   |       |

*Ile in the rat peptide

A third aspect of the invention in the administration of a combination of an ACE inhibitor and a compound of formula IV.

Examples of ACE inhibitors are those disclosed in the article by Wyvratt et al., cited above, and in the following U.S. Pat. Nos.: U.S. Pat. Nos. 4,468,519, 4,555,506, 4,374,829, 4,462,943, 4,470,973, 4,470,972, 4,350,704, 4,256,761, 4,344,949, 4,508,729, 4,512,924, 4,410,520 and 4,374,847, all incorporated herein by reference; and the following foreign patents or published patent applications:

British Specification No. 2095682 published Oct. 6, 1982 discloses N-substituted-N-carboxyalkyl aminocarbonyl alkyl glycine derivatives which are said to be angiotensin converting enzyme inhibitors and have the formula

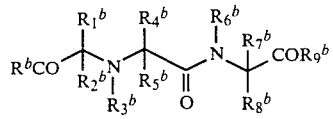

either (A) $R^b$ and $R_9^b$ are OH, 1-6C alkoxy, 2-6C alkenyloxy, di-(1-6C alkyl)amino-(1-6C) alkoxy, 1-6C hydroxyalkoxy, acylamino-(1-6C)alkoxy, acyloxy-(1-6C)alkoxy, aryloxy, aryloxy-(1-6C)alkoxy, $NH_2$, mono- or di-(1-6C alkyl)amino, hydroxyamino or aryl-(1-6C)alkylamino; $R_1^b$-$R_5^b$, $R_7^b$ and $R_8^b$ are 1-20C alkyl, 2-20C alkenyl, 2-20C alkynyl, aryl, aryl-(1-6C) alkyl having 7-12C or heterocyclyl-(1-6C)alkyl having 7-12C;

$R_6^b$ is cycloalkyl, polycycloalkyl, partly saturated cycloalkyl or polycycloalkyl, cycloalkyl-(1-6C)alkyl having 3-20C, 6-10C aryl, aryl-(1-6C)alkyl, aryl-(2-6C)alkenyl or aryl-(2-6C) alkynyl; or $R_2^b$ and $R_3^b$ together with the C an N atoms to which they are attached or $R_3^b$ and $R_5^b$ together with the N and C atoms to which they are attached form an N-heterocycle containing 3-5C or 2-4C and a S atom;

all alkyl, alkenyl and alkynyl are optionally substituted by OH, 1-6C alkoxy, thio(sic), 1-6C alkylthio, $NH_2$, mono- or di(1-6C alkyl)amino, halogen or $NO_2$;

all 'cycloalkyl' groups (including poly and partially unsaturated) are optionally substituted by halogen, 1-6C hydroxyalkyl, 1-6C alkoxy, amino-(1-6C alkyl)amino, di-(1-6C alkyl)amino, SH, 1-6C alkylthio, $NO_2$ or $CF_3$; and aryl groups are optionally substituted by OH, 1-6C alkoxy, $NH_2$, mono- or di-(1-6C alkyl) amino, SH, 1-6C alkylthio, 1-6C hydroxyalkyl, 1-6C aminoalkyl, 1-6C thioalkyl, $NO_2$, halogen, $CF_3$, $OCH_2O$, ureido or guanidino; or (B) $R^b$ and $R_9^b$ are H or 1-6C alkoxy;

$R_1^b$ and $R_2^b$ are H, 1-6C alkyl, aryl-(1-6C) alkyl having 7-12C or heterocyclyl-(1-6C) alkyl having 6-12C;

$R_3^b$-$R_5^b$, $R_7^b$ are H or 1-6C alkyl;

$R_6^b$ is cycloalkyl, polycycloalkyl, partly saturated cycloalkyl or polycycloalkyl, cycloalkyl-(1-6C) alkyl having 3-20C, aryl or aryl-(1-6C) alkyl; and aryl has 6-10C and is optionally substituted by 1-6C alkyl, 2-6C alkenyl, 2-6C alkynyl, OH, 1-6C alkoxy, $NH_2$, mono- or di-(1-6C alkyl) amino, SH, 1-6C alkylthio, 1-6C hydroxyalkyl, 1-6C aminoalkyl, 1-6C thioalkyl, $NO_2$, halogen, $CF_3$, $OCH_2O$, ureido or guanidino;

European Patent Application 0 050 800 published May 5, 1982 discloses carboxyalkyl dipeptides derivatives which are said to be angiotensin converting enzyme inhibitors and have the formula

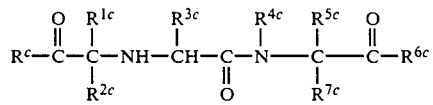

or a pharmaceutically acceptable salt thereof, wherein $R^c$ and $R^{6c}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino, lower alkylamino, dilower alkylamino, hydroxyamino, aryllower alkylamino, or substituted aryloxy or substituted aryllower alkoxy wherein the substitutent is methyl, halo or methoxy; $R^{1c}$ is hydrogen, alkyl of from 1 to 10 carbon atoms, substituted lower alkyl wherein the substitutent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2c}$ and $R^{7c}$ are the same or different and are hydrogen or lower alkyl; $R^{3c}$ is hydrogen, lower alkyl, phenyl lower alkyl, aminoethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4c}$ and $R^{5c}$ are the same or different and are hydrogen, lower alkyl or $Z^c$, or $R^{4c}$ and $R^{5c}$ taken together form a group represented by $Q^c$, $U^c$, $V^c$, $Y^c$, $D^c$ or $E^c$, wherein;

$Z^c$ is

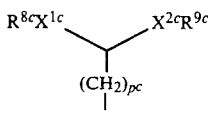

wherein $X^{1c}$ and $X^{2c}$ independent of each other are O, S or $CH_2$, $R^{8c}$ and $R^{9c}$ independent of each other are lower alkyl, lower alkenyl, lower alkynyl, cycloalkyl having 3 to 8 carbon atoms, hydroxy lower alkyl, or $—(CH_2)_{n^c}Ar^c$, wherein $n^c$ is 0, 1, 2 or 3 and $Ar^c$ is unsubstituted or substituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8c}$ and $R^{9c}$ taken together form a bridge $W^c$, wherein $W^c$ is a single bond or a methylene bridge or a substituted methylene bridge when at least one of $X^{1c}$ and $X^{2c}$ is methylene, or $W^c$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^c$ is 0, 1 or 2; with the proviso that at least one of $R^{4c}$ and $R^{5c}$ is $Z^c$, with the proviso that if $R^{4c}$ is $Z^c$ and $p^c$ is 0 then $X^{1c}$ and $X^{2c}$ must both be methylene, and with the proviso that if $X^{1c}$ and $X^{2c}$ are both methylene then $R^{8c}$ and $R^{9c}$ must form an alkylene bridge $W^c$;

$Q^c$ is

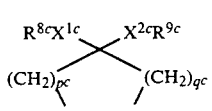

wherein $R^{8c}$, $R^{9c}$, $X^{1c}$ and $X^{2c}$ are as defined above, $p^c$ is 0, 1 or 2, $q^c$ is 0, 1 or 2, with the proviso that the sum of $p^c$ and $q^c$ must be 1, 2 or 3, with the proviso that if $p^c$ is 0 then $X^{1c}$ and $X^{2c}$ must be methylene, and with the proviso that if $X^{1c}$ and $X^{2c}$ are methylene then $R^{8c}$ and $R^{9c}$ taken together form a bridge $W^c$, wherein $W^c$ is as defined above;

$V^c$ is

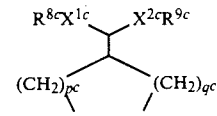

wherein $R^{8c}$, $R^{9c}$, $X^{1c}$ and $X^{2c}$ are as defined above, $p^c$ is 0, 1 or 2 and $q^c$ is 0, 1 or 2, with the proviso that the sum of $p^c$ and $q^c$ is 1, 2 or 3, with the proviso that if $X^{1c}$ and $X^{2c}$ are $CH_2$ then $R^{8c}$ and $R^{9c}$ taken together form a bridge $W^c$, wherein $W^c$ is as defined above;

$U^c$ is

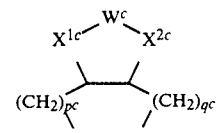

wherein $W^c$ is as defined above (except that $W^c$ may also be a methylene bridge when $X^{1c}$ and $X^{2c}$ are oxygen or sulfur), $X^{1c}$ and $X^{2c}$ are as defined above, $p^c$ is 0, 1 or 2, $q^c$ is 0, 1 or 2, with the proviso that the sum of $p^c$ and $q^c$ is 1 or 2, and with the proviso that if $p^c$ is 0, $X^{1c}$ must be $CH_2$;

$Y^c$ is

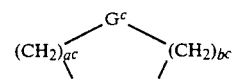

wherein $G^c$ is is oxygen, sulfur or $CH_2$, $a^c$ is 2, 3 or 4 and $b^c$ is 1, 2, 3, 4 or 5, with the proviso that the sum of $a^c$ and $b^c$ is 5, 6 or 7 or $G^c$ is $CH_2$, $a^c$ is 0, 1, 2 or 3, $b^c$ is 0, 1, 2 or 3 with the proviso that the sum of $a^c$ and $b^c$ is 1, 2 or 3, with the proviso that the sum of $a^c$ and $b^c$ may be 1, 2 or 3 only if $R^{1c}$ is lower alkyl substituted with aralkylthio or aralkyloxy;

$D^c$ is

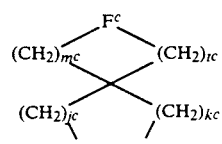

wherein $F^c$ is O or S, $j^c$ is 0, 1 or 2 and $k^c$ is 0, 1 or 2, with the proviso that the sum of $j^c$ and $k^c$ must be 1, or 3, and $m^c$ is 1, 2 or 3 and $t^c$ is 1, 2 or 3, with the proviso that the sum of $m^c$ and $t^c$ must be 2, 3 or 4;

$E^c$ is

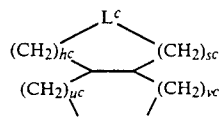

wherein $L^c$ is O or S, $u^c$ is 0, 1 or 2 and $v^c$ is 0, 1 or 2, with the proviso that the sum of $u^c$ and $v^c$ must be 1 or 2, and $h^c$ is 1 or 2 and $s^c$ is 1 or 2, with the proviso that the sum of $h^c$ and $s^c$ must be 2 or 3;

European Patent Application 0 079 522 published May 25, 1983 discloses N-carboxymethyl(amidino) lysylproline compounds which are said to be angiotensin converting enzyme inhibitors and have the formula where

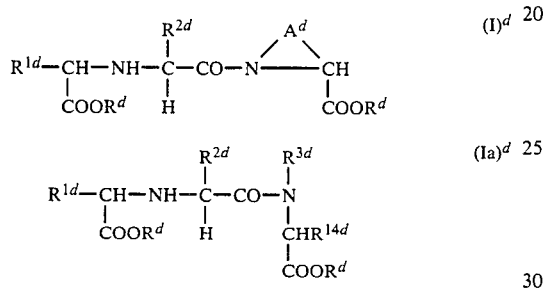

wherein:

$R^d$ and $R^{2d}$ are independently hydrogen; loweralkyl; aralkyl; or aryl;

$R^{1d}$ is hydrogen; branched or straight chain $C_{1-12}$ alkyl and alkenyl; $C_3$-$C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

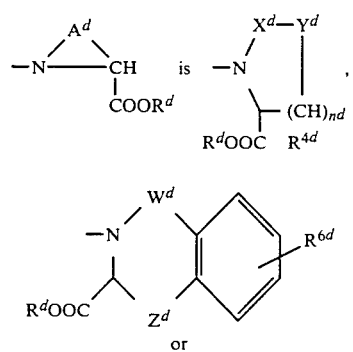

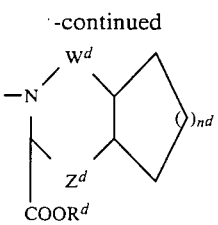

where:

$X^d$ and $Y^d$ taken together are —CH$_2$—CH$_2$—;

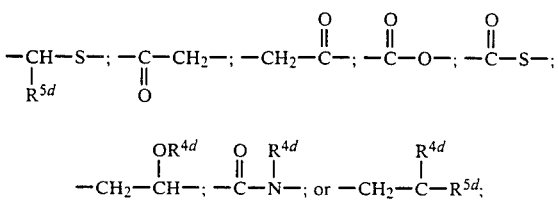

$R^{4d}$ is hydrogen; loweralkyl; aryl; substituted aryl;
$R^{5d}$ is hydrogen; loweralkyl; aryl or substituted aryl;
$n^d$ is 1 to 3;
$W^d$ is absent, —CH$_2$—; or

$Z^d$ is —(CH$_2$)$_{m^d}$, where $m^d$ is 0 to 2, provided that $m^d$ R6d is hydrogen; loweralkyl; halo; or OR4d; may not be 0 and $W^d$ may not be absent at the same time; and
$R^{6d}$ is hydrogen; loweralkyl; halo; or OR$^{4d}$;
$R^{2d}$ is —(CH$_2$)$_{r^d}$—B$^d$—(CH$_2$)$_{s^d}$—NR$^{7d}$R$^{15d}$
where
$r^d$ and $s^d$ are independently 0 to 3;
$B^d$ is absent; —O—; —S—; or —NR$^{8d}$;
where $R^{8d}$ is hydrogen; loweralkyl; alkanoyl; or aroyl; and
$R^{7d}$ is

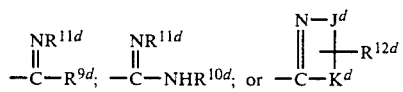

where
$R^{9d}$ is loweralkyl; aralkyl; aryl; heteroaryl; or heteroarloweralkyl and these groups substituted by hydroxy, lower alkoxy or halo; carboxyl; carboxamido; nitromethenyl.
$R^{10d}$ is is hydrogen; loweralkyl; aryl; or amidino;
$R^{11d}$ hydrogen; loweralkyl; cyano; amidino; aryl; aroyl; loweralkanoyl;

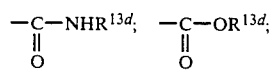

—NO$_2$; —SO$_2$NH$_2$; or SO$_2$R$^{13d}$;
$R^{12d}$ is hydrogen; loweralkyl; halo; aralkyl; amino; cyano; mono- or diloweralkylamino; or OR$^{4d}$;
$R^{13d}$ is hydrogen; loweralkyl; or aryl;
$R^{15d}$ is hydrogen; lower alkyl; aralkyl; or aryl;

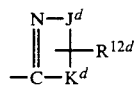

constitute a basic heterocycle of 5 or 6 atoms or benzofused analogs thereof and optionally containing 1-3N atoms, an oxygen, a sulfur, an S=O, or an SO₂ group optionally substituted by amino, lower alkyl amino, diloweralkyl amino, lower alkoxy, or aralkyl groups;

$R^{3d}$ is $C_{3-8}$ cycloalkyl and benzofused C3-8 cycloalkyl; perhydrobenzofused $C_{3-8}$ cycloalkyl; aryl; substituted aryl; heteraryl; substituted heteroaryl;

$R^{14d}$ is hydrogen or loweralkyl; and, a pharmaceutically acceptable salt thereof;

European Patent 79022 published May 18, 1983 discloses N-amino acyl-azabicyclooctane carboxylic acid derivatives which have the formula

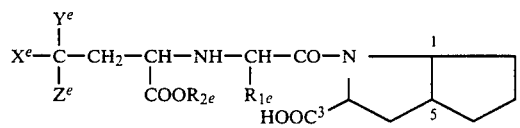

hydrogen atoms at ring positions 1 and 5 are cis to each other and the 3-carboxy group has the endo orientation;

$R^{1e}$ is H, allyl, vinyl or the side chain of an optionally protected naturally occurring α-amino acid;

$R_2^e$ is H, 1-6C alkyl, 2-6C alkenyl or aryl(1-4C alkyl);

$Y^e$ is H or OH and $Z^e$ is H, or $Y^e$ and $Z^e$ together oxygen;

$X^e$ is 1-6C alkyl, 2-6C alkenyl, 5-9C cycloalkyl, 6-12C aryl (optionally substituted by one to three 1-4C alkyl or alkoxy, OH, halo, nitro, amino (optionally substituted by one or two 1-4C alkyl), or methylenedioxy) or indol-3-yl);

European Patent 46953 published Mar. 10, 1982 discloses N-amino acyl-indoline and tetrahydro isoquinoline carboxylic acids which are angiotensin coverting enzyme inhibitors and have the formula

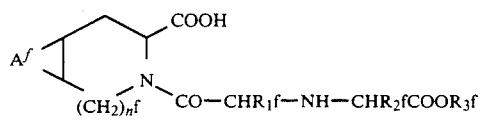

$n^f$ is 0 or 1;

is a benzene or cyclohexane ring:

$R_1^f$ and $R_2^f$ are each 1-6C alkyl, 2-6C alkenyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all $R_1^f$ and $R_2^f$ groups are optionally substituted, $R_3^f$ is H, 1-6C alkyl, 2-6C alkenyl or 7-14C aralkyl.

The following Table I lists ACE inhibitors preferred for use in the combination of this invention.

TABLE I

PREFERRED ACE INHIBITORS $$\text{R}-\overset{\text{COOR}^1}{\underset{}{\text{CH}}}-\text{NH}-\overset{\text{R}^2}{\underset{}{\text{CH}}}-\overset{\text{O}}{\underset{}{\text{C}}}-\text{R}^3$$

| | R | R₁ | R₂ | R₃ |
|---|---|---|---|---|
| spirapril | C₆H₅CH₂CH₂— | Et | CH₃ | (dithiolane-prolyl structure) |
| enalapril | C₆H₅CH₂CH₂— | Et | CH₃ | prolyl |
| ramipril | C₆H₅CH₂CH₂— | Et | CH₃ | (bicyclic prolyl structure) |
| perindopril | CH₃CH₂CH₂ | Et | CH₃ | (cyclohexane-fused prolyl structure) |

TABLE I-continued

| | | | | |
|---|---|---|---|---|
| indolapril | $C_6H_5CH_2CH_2-$ | Et | $CH_3$ | cyclohexyl-CH2 attached to -N—C—COOH |
| lysinopril | $C_6H_5CH_2CH_2-$ | H | $NH_2(CH_2)_4-$ | prolyl |
| CI-925 | $C_6H_5CH_2CH_2-$ | Et | $CH_3$ | 4,5-dimethoxybenzyl attached to -N—C—COOH (with $CH_3O$, $OCH_3$) |
| pentopril (NH = CH2) | $CH_3$ | Et | $CH_3$ | benzyl-CH2 attached to -N—C—COOH |
| cilazapril | $C_6H_5CH_2CH_2-$ | H | $\underset{CH-C-R_3=}{\overset{R_2\ \ O}{\vert\ \ \vert\vert}}$ | bicyclic diazepine with $CO_2H$ |

$$RS-CH_2-\underset{CH_3}{\overset{|}{C}}H_2-\overset{O}{\overset{\|}{C}}-R^2$$

| | R | $R_2$ |
|---|---|---|
| captopril | H | prolyl |
| zofenopril | $C_6H_5CO-$ | $SC_6H_5$-substituted pyrrolidine: -N—C—COOH |
| pivalopril | $(CH_3)_3C-\overset{O}{\overset{\|}{C}}-$ | cyclopentyl-N—CH2—COOH |

$$R-\underset{\underset{OR^1}{\vert}}{\overset{\overset{O}{\|}}{P}}-CH_2-\overset{\overset{O}{\|}}{C}-N-\underset{\underset{}{}}{\overset{R^2}{\underset{}{C}}}-COOH$$

| | R | $R^1$ | $R^2$ |
|---|---|---|---|
| fosinopril | $C_6H_5-(CH_2)_4-$ | $\underset{-CH-O-\underset{\overset{\|}{O}}{C}-CH_2CH_3}{\overset{(CH_3)_2}{\overset{\|}{CH}}}$ | $C_6H_5-$ |

We have found that the novel compounds of the present invention are effective in treating congestive heart failure and various types of hypertension, particularly volume expanded hypertension. These novel compounds as well as other mercapto-acylamino acids known in the art have been found to enhance both the magnitude and duration of the antihypertensive and natriuretic effects of endogenous ANF. Administration of a combination of a mercapto-acylamino acid and an ACE inhibitor provides an antihypertensive effect greater than either the mercapto-acylamino acid or ACE inhibitor alone. Administration of a combination of a mercapto-acylamino acid of formula IV and an exogenous ANF or ACE inhibitor is therefore particularly useful in treating hypertension.

In addition to the compound aspect, the present invention therefore also relates to treating hypertension with a mercapto-acylamino acid or with a mercapto-acylamino acid in combination with an ANF or an ACE inhibitor, which methods comprise administering to a mammal in need of such treatment an antihypertensive effective amount of the mercapto-acylamino acid or an antihypertensive effective amount of a combination of a mercapto-acylamino acid and ANF or ACE inhibitor. The drug or combination of drugs is preferably administered in a pharmaceutically acceptable carrier, e.g. for oral or parenteral administration. The combinations of drugs may be co-administered in a single composition, or components of the combination therapy may be administered separately. Where the components are administered separately, any convenient combination of dosage forms may be used, e.g. oral mercapto-acylamino acid/oral ANF, oral mercapto-acylamino acid/parenteral ACE inhibitor, parenteral mercapto-acylamino acid/oral ANF, parenteral mercapto-acylamino acid/parenteral ACE inhibitor.

When the components of a combination of a mercapto-acylamino acid and an ANF are administered separately, it is preferred that the mercapto-acylamino acid be administered first.

The present invention also relates to a pharmaceutical composition comprising a mercapto-acylamino acid for use in treating hypertension, to a pharmaceutical composition comprising both a mercapto-acylamino acid and an ANF and to a pharmaceutical composition comprising both a mercapto-acylamino acid and an ACE inhibitor.

The antihypertensive effect of mercapto-acylamino acids alone and in combination with ACE inhibitors was determined according to the following procedure:

Male Sprague Dawley rats weighing 100-150 g were anesthetized with ether and the right kidney was removed. Three pellets containing Doc acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 17-30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or mercapto-acylamino acid and blood pressure was monitored for the next 4 hours.

The antihypertensive effect of mercapto-acylamino acids in combination with ANF was determined according to the following procedures:

Male spontaneously hypertensive rats (SHR), 16-18 weeks old, 270-350 g, were anesthetized with ether and the abdominal aorta was cannulated through the tail artery. The animals were then placed into restrainers to recover from anesthesia (in less than 10 min.) and remained inside throughout the experiments. Through a pressure transducer (Gould P23 series) analog blood pressure signals were registered on a Beckman 612 recorder. A Buxco digital computer was used to obtain mean arterial pressures. Patency of the arterial cannula was maintained with a continuous infusion of 5% dextrose at 0.2 ml/hr. Animals were allowed a 90-min equilibration period. The animals first underwent a challenge with an ANF such as atriopeptin II (AP II) or AP28 30 $\mu$g/kg iv and at the end of 60 min. were treated with drug vehicle or a mercapto-acylamino acid subcutaneously. A second ANF challenge was administered 15 min. later and blood pressure was monitored for the next 90 min.

The antihypertensive effect in SHR of mercapto-acylamino acids and ACE inhibitors, alone and in combination, was determined as follows:

Animals were prepared for blood pressure measurement as described above. After stabilization, animals were dosed subcutaneously or orally with test drugs or placebo and blood pressure was monitored for the next 4 hr.

The compositions of this invention comprise a mercapto-acylamino acid or a mercapto-acylamino acid and an ANF or a mercapto-acylamino acid and an ACE inhibitor in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily antihypertensive dose of the compound or combinations of this invention is as follows: for mercapto-acylamino acids alone the typical dosage is 1 to 100 mg/kg of mammalian weight per day administered in single or divided dosages; for the combination of mercapto-acylamino acid and an ANF, the typical dosage is 1 to 100 mg of mercapto-acylamino acid/kg mammalian weight per day in single or divided dosages plus 0.001 to 0.1 mg ANF/kg of mammalian weight per day, in single or divided dosages, and for the combination of mercapto-acylamino acid and an ACE inhibitor, the typical dosage is 1 to 100 mg of mercapto-acylamino acid/kg mammalian weight per day in single or divided dosages plus 0.1 to 30 mg ACE inhibitor/kg of mammalian weight per day in single or divided dosages. The exact dose of any component or combination to be administered is determined by the attending clinician and is dependent on the potency of the compound administered, the age, weight, condition and response of the patient.

Generally, in treating humans having hypertension, the compounds or combinations of this invention may be administered to patients in a dosage range as follows: for treatment with mercapto-acylamino acids alone, about 10 to about 500 mg per dose given 1 to 4 times a day, giving a total daily dose of about 10 to 2000 mg per day; for the combination of mercapto-acylamino acid and ANF, about 10 to about 500 mg mercapto-acylamino acid per dose given 1 to 4 times a day and about 0.001 to about 1 mg ANF given 1 to 6 times a day (total daily dosage range of 10 to 2000 mg day and .001 to 6 mg/day, respectively); and for the combination of a mercapto-acylamino acid and an ACE inhibitor, about 10 to about 500 mg mercapto-acylamino acid per dose given 1 to 4 times a day and about 5 to about 50 mg ACE inhibitor given 1 to 3 times a day (total daily dosage range of 10 to 2000 mg/day and 5 to 150 mg/day, respectively). Where the components of a combination are administered separately, the number of doses of each component given per day may not necessarily be the same, e.g. where one component may have a greater duration of activity, and will therefore need to be administered less frequently.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; ceullulose and derivatives such as sodium carboxymethyl cellulose, ethyl cellulose and methyl cellulose; calcium phosphates such as dicalcium phosphate and tricalcium phosphate; sodium sulfate; calcium sufate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene gylcol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Since the present invention relates to treatment of hypertension with a combination of active ingredients wherein said active ingredients may be administered separately, the invention also relates to combining separate pharmaceutical compositions in kit form. That is, two kits are contemplated, each combining two separate units: a mercapto-acylamino acid pharmaceutical composition and an ANF pharmaceutical composition in one kit and a mercapto-acylamino acid pharmaceutical composition and an ACE inhibitor pharmaceutical composition in a second kit. The kit form is particularly advantageous when the separate components must be administered in different dosage forms (e.g. oral and parenteral) or are administered at different dosage intervals.

Following are descriptions of preparations of typical starting materials and examples of procedures for preparing compounds of formulae I-IV. Temperature designations, i.e. reaction conditions and melting points, are in °C.

PREPARATION 1

L-CYSTEINE ESTERS

Method 1:

S-(4-Methylbenzyl)-L-Cysteine, Methyl Ester, Hydrochloride

At room temperature, add thionyl chloride (2.8 ml, 2.2 equiv.) dropwise to N-t-butyloxycarbonyl-S -(4-methylbenzyl)-L-cysteine (5.0g) in methanol (500 ml) and heat the resulting mixture under reflux for 90 minutes. Cool the reaction mixture to room temperature and concentrate in vacuo to give the title compound, a white solid (4.31g), m.p. 158°-160°, $[\alpha]_D^{26} = -22.9°$ (MeOH).

By the same method, other amino acid esters are prepared:

S-Benzyl-D-cysteine ethyl ester hydrochloride, a while solid, m.p. 149°-151°, $[\alpha]_D^{26} = +15.5°$ (H$_2$O);

S-(4-Methoxybenzyl)-L-cysteine methyl ester hydrochloride, a white solid, m.p. 145°-146°, $[\alpha]_D^{26} = -23.2°$ (MeOH);

S-(3,4-Dimethylbenzyl)-L-cysteine ethyl ester hydrochloride, white solid, m.p. 161°-167°, $[\alpha]_D^{26} = -26.6°$ (MeOH); and S-t-Butyl-L-cysteine methyl ester, an oil.

Method 2: S-Phenethyl-L-Cysteine Ethyl Ester Hydrochloride

Add thionyl chloride (2.0 ml) to absolute ethanol (25 ml) at 0°-5°. To this solution add S-phenethyl-L-cysteine (2.5 g, 1.11 mmole). Warm the resulting mixture to room temperature, and then heat at 60° for 5 hours. Concentrate the reaction mixture in vacuo, dissolve the resultant residue in dichloromethane (CH$_2$Cl$_2$), and concentrate the solution in vacuo. Dissolve the residue in absolute ethanol, treat with DARCO, filter and concentrate in vacuo to give the title compound, a white solid (2.90 g) m.p. 155°-156°, $[\alpha]_D^{26} = -1.5°$ (MeOH).

By the same method, other amino acid esters are prepared:

O-Benzyl-L-tyrosine methyl ester hydrochloride, a white solid, m.p. 189-190, $[\alpha]_D^{26} = +6.9°$ (MeOH);

S-Ethyl-L-cysteine ethyl ester, an oil, $[\alpha]_D^{26} = +25.1°$ (MeOH);

S-Ethyl-L-cysteine ethyl ester hydrochloride, a white solid, mp. 130°-133° $[\alpha]_D^{26} = -11.0°$ (MeOH); and Ethionine ethyl ester, hydrochloride, clear oil, $[\alpha]_D^{26} = +15.5°$ (MeOH).

PREPARATION 2

3-Acetylthio-2-(Arylmethyl)Propionic Acids

3-Acetylthio-2-(4-phenylbenzyl)propionic acid

Step 1: 4-Biphenylmethylenemalonic acid: Heat 4-biphenyl carboxaldehyde (18.0 g, 9.89 mmole) and malonic acid (10.8 g, 10.4 mmole) in glacial acetic acid (6 ml) at approximately 100° for 2 hours. Cool the reaction mixture, dilute with dichloromethane and filter to give a white solid (8.76 g). Concentrate the filtrate, add malonic acid (1.5 g) and heat the resulting mixture at 100° for 2 hours. Cool the reaction mixture, dilute with CH$_2$Cl$_2$ and filter to give a white solid (3.44 g). Suspend the combined solids (12.20 g) in water and filter to give the title compound, a pale yellow solid (9.56 g), m.p. 208°-209° ↑.

By this method other aryl methylene malonic acids are prepared, for example:

β-Naphthylmethylene malonic acid, a white solid, m.p. 204-205°.

Step 2: (4-Phenylbenzyl)malonic acid: Hydrogenate the product of Step 1 (9.50 g, 3.5 mmole) in ethyl acetate (200 ml) in the presence of 10% palladium-on-charcoal (0.80 g) at 50 psi for 3 hours. Filter and concentrate the reaction mixture in vacuo to give the title compound, a white solid (8.16 g) m.p. 180-181°.

By this method other arylmethyl malonic acids are prepared, for example:
β-Naphthylmethyl malonic acid, a white solid, m.p. 150-152°.

Step 3: 2-(4-Phenylbenzyl)acrylic acid: Treat a portion of the product of Step 2 (4.05 g, 1.50 mmole) in water (20 ml) at 0°-5° with 40% dimethylamine in water to pH 7-8. Add the remaining product of Step 2 (4.05 g, 1.50 mmole). After 15 minutes, add aqueous formaldehyde (10.0 ml, 38%). Slowly warm the resulting mixture to room temperature and stir for 18 hours. Filter the reaction mixture, wash the white solid with water, and suspend the solid in water (150 ml). Heat this suspension at 100° for 3 hours until the solution is almost clear. Cool the solution and add concentrated hydrochloric acid to pH 2 to give a white precipitate. Filter the mixture and dry the white solid. Dissolve this white solid in hot methanol, filter and concentrate in vacuo to give the title compound, a white solid (6.68 g) m.p. 168°-170°.

By this method other 2-(aryl)acrylic acids are prepared, for example:
2-(β-naphthylmethyl)acrylic acid, a white solid, m.p. 83°-84°.

Step 4: 3-Acetylthio-2-(4-phenylbenzyl)propionic acid: Add thioacetic acid (8.0 ml) to the product of Step 3 (6.0 g, 2.77 mmole) in $CH_2Cl_2$ (30 ml) and ethyl acetate (100 ml) and stir the resulting mixture at room temperature for 72 hours. Concentrate the reaction mixture in vacuo. Dissolve the residue in toluene (100 ml), and concentrate in vacuo (3 times) to give a yellow oil (6.0 g). Chromatograph the oil on a column of silica gel (1.6 L), eluting with $CH_2Cl_2$ (4 L) $CH_2Cl_2$:methanol 1000:1 (3 L), and 1000:5 (15 L) to give the title compound, a white solid (3.44 g), m.p. 101°-103°.

By this method, other 3-acetylthio-2-(arylmethyl)-propionic acids are prepared:
3-Acetylthio-2-(4-chlorobenzyl)propionic acid, an oil.
3-Acetylthio-2-(α-naphthylmethyl)propionic acid, a white solid, m.p. 94°-97°;
3-Acetylthio-2-(β-naphthylmethyl)propionic acid, a white solid, m.p. 103°-106°;
3-Acetylthio-2-(4-methylbenzyl)propionic acid, m.p. 72°-75°; and
3-Acetylthio-2-(2-methylbenzyl)propionic acid, a waxy solid.

PREPARATION 3

1-(α-Naphthylmethyl)Acrylic Acid

Step 1: Diethyl α-naphthylmethyl malonate: Add sodium metal (11.0 g, 0.478 mole) to absolute ethanol (650 ml) with cooling and stirring until the sodium is dissolved. Add diethyl malonate (75.6 g, 0.473 mole) over 15 minutes at room temperature. After 30 min., add α-bromomethylnaphthalene (100 g, 0.452 mole) in absolute ethanol (400 ml). Heat the resulting mixture under reflux for 5 hours. Keep at room temperature for 20 hours, and concentrate in vacuo. Partition the residue between water (500 ml) and diethyl ether (700 ml). Extract the diethyl ether solution with water (200 ml), and brine (200 ml), then dry the organic layer (MgSO₄) and concentrate in vacuo to give the title compound, an oil (133.7 g).

Step 2: 3-(1-Naphthyl)-2-ethoxycarbonylpropionic acid: To the product of Step 1 (133.7 g, 0.446 mole) in absolute ethanol (400 ml) add a solution of potassium hydroxide (24.9 g, 0.445 mole) in absolute ethanol (400 ml) and stir the resulting mixture at room temperature for 20 hours. Concentrate the reaction mixture in vacuo and partition the residue between ice water (1 L) and diethyl ether (500 ml). Cool the aqueous solution to 0°-5° C. and acidify to approximately pH 2 with 2N hydrochloric acid, keeping the temperature at 0°-5°. Extract the mixture with diethyl ether, dry the organic layer (MgSO₄) and concentrate in vacuo to give the title compound, an oil (100 g).

Step 3: Ethyl 1-(α-naphthylmethyl)acrylate: Add to the product of Step 2 (100 g, 0.367 mole) and diethylamine (39 ml) a 37% aqueous solution of formaldehyde (38 ml) over 30 min. at 0°-5° C. with vigorous stirring. Stir the mixture at room temperature for 7 hours and then extract with diethyl ether (3×500 ml). Extract the organic layer with 2N hydrochloric acid (2×500 ml), saturated aqueous sodium bicarbonate solution (500 ml) and brine (500 ml). Dry the organic layer (MgSO₄) and concentrate in vacuo to give the title compound, an oil (58.6 g).

Step 4: 1-(α-Naphthylmethyl)acrylic acid: Treat the product of Step 3 (12.0 g, 50 mmole) in dioxane (50 ml) with 1N sodium hydroxide (60 ml) and stir the resulting mixture at room temperature for 18 hours. Concentrate the reaction mixture under nitrogen, dilute with water and extract with ethyl acetate. Cool the aqueous solution to 0°-5° and add concentrated hydrochloric acid slowly to pH 3-4 to give a white solid. Filter the reaction mixture, wash the resultant white solid with water and dry to give the title compound, a white solid (9.62 g), m.p. 115°-117°.

PREPARATION 4

L-Bishomophenylalanine t-Butyl Ester
[(2S)-Amino-5-Phenylpentanoic Acid, t-Butyl Ester]

Step 1: 4-Benzoyl-2(S)-trifluoroacetamidobutyric acid: Heat at reflux for 3 hours a mixture of N-trifluoroacetyl-L-glutamic anhydride (18.0 g, 80 mmol) and AlCl₃ (23.5 g, 177 mmol) in dry benzene (400 ml). Allow to cool, treat with ice (400 ml), conc. HCl (100 ml), and ethyl acetate (EtOAc) (400 ml). Dry the organic layer and concentrate to obtain the title compound as a brown crystalline solid (25 g).

Step 2: 5-Phenyl-2(S)-trifluoroacetamidopentanoic acid: Reduce the product of Step 1 (9.7 g) with Pearlman's catalyst (3.5 g) in EtOAc (75 ml) and ethanol (25 ml) at 50 psi H₂ for 3 hours. Filter, concentrate and wash the resultant residue with 3:1 hexane:diethyl ether to give the title compound (7.8 g).

Step 3: N-Trifluoroacetyl-L-bishomophenylalanine, t-butyl ester: Treat the product of Step 2 (11.3 g) with isobutylene (25 ml) and conc. H₂SO₄ (1.0 ml) in CH₂Cl₂ (100 ml) for 16 hours. Partition between diethyl ether and 1N NaHCO₃, dry, concentrate, and chromatograph the resultant residue on silica gel, eluting with 2:1 hexane:diethyl ether to obtain 11.3 g of the title compound as a colorless oil.

Step 4: L-Bishomophenylalanine, t-butyl ester, hydrochloride: To the product to Step 3 in EtOH (120 ml) add NaBH₄ (5.2 g) portionwise over 30 min. Stir another 1.5 hours, concentrate, and partition between diethyl ether and H$_2$O. Dry and concentrate to obtain an oil (8.1 g). Treat with HCl:diethyl ether to give the hydrochloride salt of the title compound, white crystals (4.0 g), m.p. 161°–162°, $[\alpha]_D^{26}$ = +15.6° (MeOH, c=0.5).

PREPARATION 5

S-(4-Methylbenzyl)-L-Cysteine Amide

Step 1: N-t-Butyloxycarbonyl-S-(4-methylbenzyl)-L-cysteine amide: React N-t-butyloxycarbonyl-S-(4-methylbenzyl)-L-cysteine (6.50 g) with triethylamine (4.44 g, 6.16 ml) in tetrahydrofuran (THF). Cool the mixture to 0°–5°. Add ethyl chloroformate (4.77 g, 3.41 ml) in THF (5 ml) dropwise over 5 min. and stir the reaction mixture for 15 min. Add ammonium hydroxide (28%, 2.0 ml) in THF (5 ml) dropwise. Allow the reaction mixture to warm to room temperature and stir for 18 hr. Filter the reaction mixture and concentrate the filtrate in vacuo to give a pale yellow solid. Dissolve this solid in CH$_2$Cl$_2$ and extract with H$_2$O. Concentrate the dried (MgSO$_4$) CH$_2$Cl$_2$ solution in vacuo to give a pale yellow solid (6.41 g). Recrystallize this solid from EtOAc to give the title compound, a white solid (2.82 g), m.p. 140°–141°, $[\alpha]_D^{26}$ = −7.5° (MeOH).

Step 2: S-(4-Methylbenzyl)-L-cysteine amide: Treat the product of Step 1 (2.79 g) in CH$_2$Cl$_2$ (40 ml) with trifluoroacetic acid (10 ml) at room temperature for 18 hr. Concentrate the reaction mixture in vacuo. Dissolve the residue in CH$_2$Cl$_2$ and concentrate in vacuo (twice). Dissolve the white solid in EtOAc and extract with 10% sodium bicarbonate solution. Dry (MgSO$_4$) the EtOAc and concentrate in vacuo to give the title compound, a white solid (1.53 g) m.p. 94°–95°, $[\alpha]_D^{26}$ = −1.3° (MeOH).

PREPARATION 6

S-(4-Methylbenzyl)-L-Cysteine t-Butyl Ester

To a cold solution of isobutylene (50 ml) in dioxane (80 ml), add S-(4-methylbenzyl)-L-cysteine (5.0 g) and concentrated H$_2$SO$_4$ (10 ml). Seal the vessel, allow to warm to room temperature, and stir for 18 hr. Pour into 5% NaOH (500 ml), extract with Et$_2$O (3×400 ml), dry (MgSO$_4$) and concentrate the Et$_2$O in vacuo to give an oil. Treat the oil with HCl in Et$_2$O to give the title compound, white needles (2.76 g) m.p. 218° (dec).

EXAMPLE 1

N-(2-Benzyl-3-Mercaptopropionyl)-S-(4-Methylbenzyl)-L-Cysteine (Isomers A and B)

Step 1: N-(3-Acetylthio-2-Benzylpropionyl)-S-(4-Methylbenzyl)-L-Cysteine Methyl Ester (Isomers A & B): Add S-(4-methylbenzyl)-L-cysteine methyl ester, hydrochloride (1.85 g, 0.77 mmole) to 3-acetylthio-2-benzyl propionic acid (1.93 g, 0.81 mmole), DEC (1.46 g, 0.76 mmole), HOBT (1.18 g, 0.76 mmole) and NMM (2.30 g, 2.5 ml, 2.27 mmole) in DMF (20 ml) and stir the resulting mixture at room temperature for 20 hours. Concentrate the reaction mixture in vacuo and partition the residue between EtOAc and water. Concentrate the dried (MgSO$_4$) ethyl acetate solution in vacuo to give an amber oil (3.85 g). Chromatograph the oil on silica gel (Baker, 60–200 mesh) (1.5 L) using EtOAc:hexane 4:21 as eluent to give Isomer A, white solid (0.64 g), m.p. 101°104°, $[\alpha]_D^{26}$ = −76.2° (MeOH); overlap Isomer A and Isomer B (0.40 g); and Isomer B, white solid (0.67 g), mp. 52°–55° $[\alpha]_D^{26}$ = −4.9° (MeOH).

Step 2: N-(2-Benzyl-3-Mercaptopropionyl)-(S)-(4-Methylbenzyl)-L-Cysteine (Isomer B): Dissolve Isomer B (0.66 g, 1.6 mmole) in methanol (20 ml) under a nitrogen atmosphere, cool to 0°–5°, add 1N sodium hydroxide (4.8 ml), stir the mixture at 0°–5° for 6 hours and then keep at that temperature for 18 hours. Concentrate the reaction mixture under nitrogen, dilute the resultant oil with water (200 ml) and ethyl acetate (200 ml) and acidify to pH 2–4 with 1N hydrochloric acid. Dry (MgSO$_4$) the ethyl acetate solution and concentrate in vacuo to give the title compound (Isomer B), a viscous oil (0.45g), $[\alpha]_D^{26}$ = −56.3° (MeOH).

Step 3: N-(2-Benzyl-3-Mercaptopropionyl)-(S)-(4-Methylbenzyl)-L-Cysteine (Isomer A): By a procedure similar to that of Step 2 react Isomer A (0.63 g) and 1N sodium hydroxide (4.5 ml) to give the title compound (Isomer A), a viscous clear oil (0.165 g), $[\alpha]_D^{26}$ = −8.8° (MeOH).

In a similar manner, according to Example 1, Step 1, using the appropriate propionic acid, prepare:

N-[3-Acetylthio-2-(α-naphthylmethyl)propionyl]-S-(4-methylbenzyl)-L-cysteine ethyl ester, Isomer A, m.p. 71°–74°, $[\alpha]_D^{26}$ = −40.6° (MeOH);

N-[3-Acetylthio-2-(α-naphthylmethyl)propionyl]-S-(4-methylbenzyl)-L-cysteine ethyl ester, Isomer B, m.p. 88°–90°, $[\alpha]_D^{26}$ = −58.8° (MeOH);

N-[3-Acetylthio-2(β-naphthylmethyl)propionyl]-S-(4-methylbenzyl)-L-cysteine ethyl ester, Isomer A, m.p. 74°–77°, $[\alpha]_D^{26}$ = −61.0° (MeOH);

N-[3-Acetylthio-2(β-naphthylmethyl)propionyl]-S-(4-methylbenzyl)-L-cysteine ethyl ester, Isomer B, m.p. 86°–88°, $[\alpha]_D^{26}$ = −20.7° (MeOH);

N-[3-Acetylthio-2-(4-chlorobenzyl)propionyl]-S-benzyl-L-cysteine ethyl ester (Isomer A), m.p. 89°–90°;

N-[3-Acetylthio-2-(4-chlorobenzyl)propionyl]-S-benzyl-L-cysteine ethyl ester (Isomer B), m.p. 103°–104°; and N-[3-Acetylthio-2-(4-chlorobenzyl)propionyl]-L-tryptophan methyl ester (Isomers A and B).

Using the procedure of Example 1, Step 2, treat the above 3-acetylthio compounds to obtain the following 3-mercaptopropionyl compounds:

N-[2-(α-Naphthylmethyl)-3-mercaptopropionyl]-S-(4-methylbenzyl)-L-cysteine Isomer A, m.p. 70°–75°, $[\alpha]_D^{26}$ = +18.3° (MeOH);

N-[2-(α-Naphthylmethyl)-3-mercaptopropionyl]-S-(4-methylbenzyl)-L-cysteine Isomer B, m.p. 48°–55°, $[\alpha]_D^{26}$ = −102.3° (MeOH);

N-[2-(β-Naphthylmethyl)-3-mercaptopropionyl]-S-(4-methylbenzyl)-L-cysteine, Isomer A, a white foam, $[\alpha]_D^{26}$ = +9.9° (MeOH);

N-[2-(ß-Naphthylmethyl)-3-mercaptopropionyl]-S-(4-methylbenzyl)-L-cysteine, Isomer B, a white foam, $[\alpha]_D^{26}$ = −50.1° (MeOH);

N-[2-(4-chlorobenzyl)-3-mercaptopropionyl]-S-benzyl-L-cysteine (Isomer A), $[\alpha]_D^{26}$ = −3.0° (EtOH, c=1);

N-[2-(4-chlorobenzyl)-3-mercaptopropionyl]-S-benzyl-L-cysteine (Isomer B), $[\alpha]_D^{26}$ = −48.7° (EtOH, c=1);

N-[2-(4-chlorobenzyl)-3-mercaptopropionyl]-L-tryptophan (Isomer A), $[\alpha]_D^{26}$ = +18.1° (EtOH, c=0.5); and N-[2-(4-chlorobenzyl)-3-mercaptopropionyl]-L-tryptophan (Isomer B), $[\alpha]_D^{26}$ = −22.5° (EtOH, c=0.5).

EXAMPLE 2

N-(2-Benzyl-3-Mercaptopropionyl)-S-Benzyl-L-Cysteine (Isomers A & B)

Step 1: N-(3-Acetylthio-2-Benzylpropionyl)-S-Benzyl-L-Cysteine, Ethyl Ester (Isomers A & B): React S-benzyl-L-cysteine ethyl ester hydrochloride (1.38 g) and 3-acetylthio-2-benzyl propionic acid (1.19 g) in a procedure similar to that described in Example 1, Step 1 to give a yellow oil. Chromatograph the oil on silica gel (1.5 L, 60–200 mesh) using $CH_2Cl_2$ ethyl acetate 98:2 as eluant to give Isomer A, white solid (0.49 g), m.p. 83°–85°, $[\alpha]_D^{26} = -73.5°$ (MeOH); overlap Isomer A and B (0.66 g); and Isomer B, white solid, m.p. 72°–74°, $[\alpha]_D^{26} = -9.4°$ (MeOH).

Step 2: Using the procedure described in Example 1, Step 2, separately treat the Isomers of Step 1 above to obtain Isomers A and B of the title compound: Isomer A, a colorless oil, $[\alpha]_D^{26} = +13.5°$ (MeOH), and Isomer B, a colorless oil, $[\alpha]_D^{26} = +38.2°$ (MeOH).

EXAMPLE 3

N-(2-Benzyl-3-Mercaptopropionyl)-S-(4-Methoxybenzyl)-L-Cysteine (Isomers A and B)

Step 1: N-(3-Acetylthio-2-Benzylpropionyl)-S-Benzyl-D-Cysteine, Ethyl Ester (Isomers A and B): React S-benzyl-D-cysteine ethyl ester hydrochloride (2.05 g) and 3-acetylthio-2-benzylpropionic acid (1.77 g) in a manner similar to that described in Example 1, Step 1 to give a light amber oil. Place the oil on a column of silica gel 2 L, 60–200 mesh) and elute with $CH_2Cl_2$:ethyl acetate 98:2 to give Isomer A, white solid (0.70 g), m.p. 84°–85°; $[\alpha]_D^{26} = +75.9°$ (MeOH); overlap Isomer A and Isomer B (0.85 g); and Isomer B, white solid (0.33 g), $[\alpha]_D^{26} = +15.6°$ (MeOH).

Step 2: Using the procedure described in Example 1, Step 2, separately treat the Isomers of Step 1 above to obtain Isomers A and B of the title compound: Isomer A, a colorless oil $[\alpha]_D^{26} = +13.5°$ (MeOH); and Isomer B, a colorless oil, $[\alpha]_D^{26} = +38.2°$ (MeOH).

EXAMPLE 4

N-(2-Benzyl-3-Mercaptopropionyl)-S-(4-Methoxybenzyl)-L-Cysteine (Isomers A and B)

Step 1: N-(3-Acetylthio-2-Benzylpropionyl)-S-(4-Methoxybenzyl)-L-Cysteine Methyl Ester (Isomers A and B) React S-(4-methoxybenzyl)-L-cysteine methyl ester hydrochloride (1.85 g) and 3-acetylthio-2-benzylpropionic acid (1.95 g) in the manner described in Example 1, Step 1 to give an amber oil. Chromatograph this oil on a column of silica gel (2 L, 60–200 mesh) and elute with ethyl acetate:hexane 5:20 to give Isomer A, a clear oil (0.63 g), $[\alpha]_D^{26} = -66.5°$ (MeOH), overlap Isomer A and Isomer B (0.28 g); and Isomer B, a clear oil (0.67 g), $[\alpha]_D^{26} = +3.0°$ (MeOH).

Step 2: Using the procedure described in Example 1, Step 2 separately treat the isomers of Step 1 above to obtain Isomers A and B of the title compound: Isomer A, a viscous oil, $[\alpha]_D^{26} = -19.3°$ (MeOH); and Isomer B, a viscous oil, $[\alpha]_D^{26} = -44.2°$ (MeOH).

EXAMPLE 5

N-(2-Benzyl-3-Mercaptopropionyl)-S-(3,4-Dimethylbenzyl)-L-Cysteine (Isomers A And B)

Step 1: N-(3-Acetylthio-2-Benzylpropionyl)-S-(3,4-Dimethylbenzyl)-L-Cysteine Ethyl Ester (Isomers A and B): React S-(3,4-dimethylbenzyl)-L-cysteine ethyl ester hydrochloride (2.20 g) and 3-acetylthio-2-benzylpropionic acid (1.74 g) in the manner described in Example 1, Step 1 to give an amber oil. Place the oil on a column of silica gel (1 L) and elute with ethyl acetate:hexane 25:170 (4 L) and then methanol:hexane 25:170 to give a light orange oily solid. Repeat the chromatography to give Isomer A, a white solid (0.52 g), m.p. 89.5°–92.5°, $[\alpha]_D^{26} = -71.1°$ (MeOH) and Isomer B, a white solid (0.60 g), m.p. 51°–55°, $[\alpha]_D^{26} = -8.4°$ (MeOH).

Step 2: Using the procedure described in Example 1, Step 2, separately treat the Isomers of Step 1 above, to obtain Isomers A and B of the title compound: Isomer A, a clear viscous oil, $[\alpha]_D^{26} = -18.0°$ (MeOH); and Isomer B, a clear viscous oil, $[\alpha]_D^{26} = -56.5°$ (MeOH).

EXAMPLE 6

N-(2-Benzyl-3-Mercaptopropionyl)-S-Phenethyl-L-Cysteine (Isomers A And B)

Step 1: N-(3-Acetylthio-2-Benzylpropionyl)-S-Phenethyl-L-Cysteine Ethyl Ester, (Isomers A and B): React S-phenethyl-L-cysteine ethyl ester hydrochloride (2.85 g) and 3-acetylthio-2-benzylpropionic acid, (2.38 g) in a manner similar to that described in Example 1, Step 1 to give an amber oil. Chromatograph this oil on Prep 500 (2 silica gel cartridges) and elute with $CH_2Cl_2$ (4 L) and then $CH_2Cl_2$:ethyl acetate 100:2 to give Isomer A, a white solid (1.32 g), m.p. 63°–64°, $[\alpha]_D^{26} = -51.2°$ (MeOH); overlap Isomer A and Isomer B (0.63 g); and Isomer B, white solid (1.14 g), m.p. 84°–86°, $[\alpha]_D^{26} = +5.3°$ (MeOH).

Step 2: Using the procedure described in Example 1, Step 2, separately treat Isomers A and B of Step 1 above to obtain Isomers A and B of the title compound. Isomer A, a colorless oil, $[\alpha]_D^{26} = +4.8°$ (MeOH); and Isomer B, a colorless oil, $[\alpha]_D^{26} = -39.7°$ (MeOH).

EXAMPLE 7

N-(2-Benzyl-3-Mercaptopropionyl)-S-(t-Butyl)-L-Cysteine (Isomers A and B)

Step 1: N-(3-Acetylthio-2-Benzylpropionyl)-S-(t-Butyl)-L-Cysteine Methyl Ester (Isomers A and B): React S-(t-butyl)-L-cysteine methyl ester (2.32 g) and 3-acetylthio-2-benzylpropionic acid (3.22 g) in the manner described in Example 1, Step 1 to give an orange solid. Chromatograph this solid on a column of silica gel (2 L, 60–200 mesh) and elute with ethyl acetate:hexane 3:17 to give Isomer A, a clear oil (1.09 g), $[\alpha]_{26} = -44.9°$ (MeOH); overlap Isomer A and Isomer B (0.52 g); and Isomer B, a clear oil (0.75 g), $[\alpha]_D^{26} = +8.3°$ (MeOH).

Step 2: Using the procedure described in Example 1, Step 2, separately treat the Isomers above to obtain Isomers A and B of the title compound; Isomer A, a clear viscous oil, $[\alpha]_D^{26} = +0.4°$ (MeOH), and Isomer B, a white solid, m.p. 68°–75°, $[\alpha]_D^{26} = -32.3°$ (MeOH).

EXAMPLE 8

N-(2-Benzyl-3-Mercaptopropionyl)-L-Ethionine (Isomers A and B)

Step 1: N-(3-Acetylthio-2-Benzylpropionyl)-L-Ethionine Ethyl Ester (Isomers A and B): React L-ethionine ethyl ester (3.51 g) and 3-acetylthio-2-benzylpropionic acid (4.37 g) in a manner similar to that described in Example 1, Step 1 to give a yellow residue. Chromatograph the yellow residue on the Waters Prep 500 (2 silica gel cartridges) and elute with ethyl acetate:hexane 2:18 (16 L), then ethyl acetate:hexane 3:17. Repeat chromatography of the fractions using ethyl acetate:hexane as eluant to give Isomer A, a white solid (0.89 g), m.p. 84°–90°, $[\alpha]_D^{26} = -60.6°$ (MeOH) and Isomer B (0.82 g), m.p. 79°–84°, $[\alpha]_D^{26} = -0.3°$ (MeOH).

Step 2: Using the procedure described in Example 1, Step 2, separately treat the Isomers of Step 1 above to obtain Isomers A and B of the title compound; Isomer A, a milky viscous oil, $[\alpha]_D^{26} = -41.8°$ (MeOH); and Isomer B, a milky viscous oil, $[\alpha]_D^{26} = -66.0°$ (MeOH).

EXAMPLE 9

N-(2-Benzyl-3-Mercaptopropionyl)-0-Benzyl-L-Tyrosine (Isomers A and B)

Step 1: N-(3-Acetylthio-2-benzylpropionyl)-O-benzyl-L-tyrosine Methyl Ester (Isomers A and B): React O-benzyl-L-tyrosine methyl ester hydrochloride (2.77 g) and 3-acetylthio-2-benzylpropionic acid (2.05 g) in a manner similar to that described in Example 1, Step 1 to give a yellow-orange oil. Chromatograph this oil on a column of silica gel (2.5 L) and elute with CH$_2$Cl$_2$:ethyl acetate 98:2 to give Isomer A, a white solid (0.84 g) m.p. 108°–109°; $[\alpha]_D^{26} = -39.8°$ (MeOH); overlap Isomer A and Isomer B (0.80 g); and Isomer B, white solid (0.45 g), m.p. 92–93°, $[\alpha]_D^{26} = +19.2°$ (MeOH).

Step 2: Using the procedure described in Example 1, Step 2, separately treat the Isomers of Step 1 above to obtain Isomers A and B of the title compound: Isomer A, an off-white solid, $[\alpha]_D^{26} = +4.8°$ (MeOH); and Isomer B, a viscous colorless oil $[\alpha]_D^{26} = +2.4°$ (MeOH).

EXAMPLE 10

N-(2-Benzyl-3-Mercaptopropionyl)-(S)-Bishomophenyl Alanine (Isomers A and B)

Step 1: N-(3-Acetylthio-2-Benzylpropionyl)-(S)-Bishomophenylalanine t-Butyl Ester (Isomers A and B): React (S)-bishomophenylalanine t-butyl ester hydrochloride (2.49 g) and 3-acetylthio-2-benzylpropionic acid (2.39 g) in the manner described in Example 1, Step 1 to give a yellow oil. Chromatograph this oil on Waters Prep 500 (2 silica gel cartridges) and elute with CH$_2$Cl$_2$ (4 L) and then CH$_2$Cl$_2$:ethyl acetate 100:2 to give Isomer A, a colorless oil (0.99 g), $[\alpha]_D^{26} = -54.7°$ (MeOH), overlap Isomer A and Isomer B (0.62 g); and Isomer B, a colorless oil (0.79 g), $[\alpha]_D^{26} = +5.1°$ (MeOH).

Step 2: N-(3-Acetylthio-2-Benzylpropionyl)-(S)-Bishomophenylalanine (Isomer A and B): To Isomer A of the product of Step 1 (0.97 g, 0.21 mmole) in CH$_2$Cl$_2$ (10 ml) at 0°–5°, add dropwise trifluoroacetic acid (10 ml). Warm the resulting mixture to room temperature, stir for 18 hours, and concentrate in vacuo. Dissolve the residue in CH$_2$Cl$_2$ (10 ml) and concentrate in vacuo. Treat the residue with diethyl ether (10 ml) and concentrate in vacuo to give Isomer A of the title compound, a light amber oil (0.87 g), $[\alpha]_D^{26} = -43.0°$ (MeOH).

By this same method, convert Isomer B of Step 1 to N-(3-acetylthio-2-benzylpropionyl)-(S)-bishomophenylalanine Isomer B, a light amber oil, $[\alpha]_D^{26} = +19.6°$ (MeOH).

Step 3: N-(2-Benzyl-3-Mercaptopropionyl)-(S)-Bishomophenylalanine (Isomers A and B): Dissolve Isomer A of Step 2 in methanol (15 ml) at 0°–5° under a nitrogen atmosphere and treat with 1N sodium hydroxide (6.3 ml). Treat the resulting mixture as described in Example 1, Step 2, to give Isomer A of the title compound, a pale yellow viscous oil (0.69 g), $[\alpha]_D^{26} = -25.4°$ (MeOH).

By this same method, convert Isomer B of Step 2 to N-(2-benzyl-3-mercaptopropionyl)-(S)-bishomophenylalanine Isomer B, a pale yellow viscous oil, $[\alpha]_D^{26} = -50.0°$ (MeOH).

In a similar manner, substitute (S)-(4-methylbenzyl)-L-cysteine t-butyl ester (Preparation 6) for (S)-bishomophenylalanine in Example 10, Step 1 to obtain N-(3-acetylthio-2-benzylpropionyl)-(S)-(4-methylbenzyl)-L-cysteine t-butyl ester, Isomer A, $[\alpha]_D^{26} = -82.8°$ (MeOH); and
N-(3-acetylthio-2-benzylpropionyl)-(S)-(4-methylbenzyl)-L-cysteine t-butyl ester, Isomer B, $[\alpha]_D^{26} = -23.5°$ (MeOH).

Treat the above esters in a manner similar to that described in Example 10, Step 2 to obtain
N-(3-acetylthio-2-benzylpropionyl)-(S)-(4-methylbenzyl)-L-cysteine, Isomer A, $[\alpha]_D^{26} = -58.8°$ (MeOH); and
N-(3-acetylthio-2-benzylpropionyl)-(S)-(4-methylbenzyl)-L-cysteine, Isomer B, $[\alpha]_D^{26} = -6.6°$ (MeOH).

EXAMPLE 11

N-[3-Mercapto-2(R,S)-Benzylpropionyl]-L-Methionine

Step 1: N-[3-Acetylthio-2(R,S)-Benzylpropionyl]-L-Methionine Methyl Ester: Add methionine methyl ester (2.00 g, 1.23 mmole) to 3-acetylthio-2-benzylpropionic acid (3.01 g, 1.26 mmole), DEC (2.34 g, 1.22 mmole), HOBT (1.88 g, 1.23 mmole) and NMM (2.34 g, 2.31 mmole) in DMF (12 ml), and treat the resulting mixture as described in Example 1, Step 1 to give an amber oil (4.36 g). Chromagraph the oil on a column of silica gel (1 L 60–200 mesh) elute with CH$_2$Cl$_2$ (1 L) and then CH$_2$Cl$_2$:ethyl acetate 99:1 to give the title compound, a clear oil (2.61 g), $[\alpha]_D^{26} = -38.9°$ (MeOH).

Step 2: N-[3-Mercapto-2(R,S)-Benzylpropionyl]-L-Methionine: Dissolve the product of Step 1 in methanol (20 ml) and treat with 1N NaOH (20.4 ml) as described in Example 1, Step 2 to give the title compound, a white solid, m.p. 132°–135°, $[\alpha]_D^{26} = -34.6°$ (MeOH).

Using the method of Example 11, Step 1, other N-[3-(R,S)-Acetylthio-2-benzylpropionyl]amino acid esters are prepared:

N-[3-Acetylthio-2(R,S)-benzylpropionyl]-S-methyl-L-cysteine ethyl ester, a clear oil, $[\alpha]_D^{26} = -25.9°$ (MeOH);

N-[3-Acetylthio-2(R,S)-benzylpropionyl]-S-trityl-L-cysteine methyl ester, an amber oil, $[\alpha]_D^{26} = +5.9°$ (MeOH); and N-[3-Acetylthio-2(R,S)-benzylpropionyl]-(S)-tryptophan methyl ester, a colorless oil, $[\alpha]_D^{26} = -14.7°$ (MeOH).

Similarly, from 3-benzoylthio-2(S)-benzylpropionic acid, prepare N-(3-benzoylthio-2(S)-benzylpropionyl)-S-methionine methyl ester, a white solid, m.p. 78°–80° C., $[\alpha]_D^{26} = -67.9°$ (EtOH, c=1).

Using the procedure of Example 11, Step 2, convert the above acetylthio and benzoylthio compounds to the following 3-mercaptopropionyl compounds:

N-[2(R,S)-Benzyl-3-mercaptopropionyl]-S-methyl-L-cysteine, a clear viscous oil, $[\alpha]_D^{26} = -31.1°$ (MeOH);

N-[2(R,S)-Benzyl-3-mercaptopropionyl]-S-trityl-L-cysteine, a white solid, $[\alpha]_D^{26} = +10.5°$ (MeOH);

N-[2(R,S)-Benzyl-3-mercaptopropionyl]-(S)-tryptophan, a white foam, m.p. 68°–69°, $[\alpha]_D{}^{26} = -0.5°$ (MeOH); and N-[2(S)-Benzyl-3-mercaptopropionyl]-S-methionine, a white solid, m.p. 88°–89°.

EXAMPLE 12

N-[2-(4-Phenylbenzyl)-3-Mecaptopropionyl]-S-(4-Methylbenzyl)-L-Cysteine (S,R and R,R Diastereomers)

Step 1: 3-Acetylthio-2-(4-Phenylbenzyl)Propionyl Chloride: To 3-acetylthio-2-(4-phenylbenzyl)propionic acid (3.39 g, 10.8 mmole) in toluene (25 ml) add 1% DMF in toluene (2 drops) and thionyl chloride (1.2 ml, 1.65 g, 13.8 mmoles) and stir the resulting solution at room temperature for 18 hours. Concentrate the reaction mixture in vacuo, dissolve the residue in toluene (100 ml) and concentrate the solution in vacuo to give the title compound, a light brown oil (3.37 g).

Step 2: N-[3-Acetylthio-2-(4-Phenylbenzyl)Propionyl]-S-(4-Methylbenzyl)-L-Cysteine (S,R and R,R diastereomers): Add the acid chloride (3.37 g) from Step L-cysteine hydrochloride (2.62 g, 10 mmol) in acetonitrile (30 ml), water (15 ml) and triethylamine (2.8 ml), and stir the resulting mixture at room temperature for 4 hours. Concentrate the reaction mixture in vacuo and partition the residue between ethyl acetate (700 ml) and water (2×200 ml) and then saturated sodium chloride solution (100 ml). Dry the ethyl acetate solution (MgSO4) and concentrate in vacuo to give a brown solid. Chromatograph this solid on a column of silica gel (2 L, 60-200 mesh) and elute with CH2Cl2:methanol:glacial acetic acid (97.5:2.5:0.25) to give a white foam (2.45 g). Chromatograph this white foam on a column of silica gel (1.2 L, 60-200 mesh) and elute with CH2Cl2:methanol:glacial acetic acid (97.5:2.5:0.25) to give the S,R-diastereomer of title compound, a white solid (1.04 g), m.p. 123°–125°, $[\alpha]_D{}^{26} = -45.5°$ (EtOH) and the R,R-diastereomer of the title compound, a white solid (0.86 g), m.p. 131°–135°, $[\alpha]_D{}^{26} = -7.1°$ (MeOH).

Using a similar procedure, prepare the diastereomers of the following:

N-[3-acetylthio-2-benzylpropionyl]-S-(4-methylbenzyl)-L-cysteine: the S,R-diastereomer, a colorless oil, $[\alpha]_D{}^{26} = -23.0°$ (MeOH) and the R,R-diastereomer, a yellow oil, $[\alpha]_D{}^{26} = -1.3°$ (MeOH);

N-(2-acetythiomethyl-3-(4-methylphenylpropionyl)-S-methionine: the S,S-diastereomer, a white solid, m.p. 90°–93°, $[\alpha]_D{}^{26} = -32.2°$ (EtOH, c=1) and the R,S-diastereomer, a white solid, $[\alpha]_D{}^{26} = +13.0°$ (EtOH, c=1);

N-(2-acetylthiomethyl-3-phenylpropionyl)-S-methionine: the S,S-diastereomer, a white solid, m.p. 95°–98°, $[\alpha]_D{}^{26} = -36.6°$ (EtOH, c=1).

Step 3: N-[2-(4-Phenylbenzyl)-3-Mercaptopropionyl]-S-(4-Methylbenzyl)-L-Cysteine (S,R and R,R-diastereomers): Dissolve the S,R-diastereomer of Step 2 in methanol saturated with ammonia (50 ml) at 0°–5° under a nitrogen atmosphere. After 35 minutes, bubble nitrogen through the reaction mixture. Dilute the reaction mixture with water and acidify to pH 2–4 with 1N hydrochloric acid. Extract the acidic solution with ethyl acetate, dry the organic layer (MgSO4) and concentrate in vacuo to give the S,R-diastereomer of the title compound, a white solid (0.73 g). Purify the S,R-diastereomer by flash chromatography on silica gel (Baker flash silica gel, 40 μm) (25 g) eluting with CHCl2:MeOH:gl.AcOH, 97.5:2.5:0.25, to obtain a white solid (0.549 g), $[\alpha]_D{}^{26} = -2.2°$ (MeOH).

In a similar fashion, prepare the R,R-diastereomer of the title compound, a white solid, $[\alpha]_D{}^{26} = -62.2°$ (MeOH).

EXAMPLE 13

N-[2-Benzyl-3-Mercaptopropionyl]-L-Methionine Amide

Step 1: N-(3-Acetylthio-2-Benzylpropionyl)-L-Methionine Amide: In similar fashion to that described in Example 12, Step 2, convert L-methionine amide to N-(3-acetylthio-2-benzylpropionyl)-L-methionine amide. Recrystallize from hexane:CH2Cl2 to obtain a solid, m.p. 101°–3°. Chromatograph on silica gel with 4% methanol/CH2Cl2 to obtain the S,S-diastereomer, m.p. 149°–151°, $[\alpha]_D{}^{26} = -87.5°$ (CHCl3) and the R,S-diastereomer, m.p. 119°–121°, $[\alpha]_D{}^{26} = +5.0°$ (CHCl3).

Step 2: N-(2-Benzyl-3-Mercaptopropionyl)-L-Methionine Amide: Treat each of the 3-acetylthio diastereomers of Step 1 with NH3/MeOH for 4 hours as in Example 12, Step 3, to give the S,S-diastereomer of the title compound, $[\alpha]_D{}^{26} = -67.8°$ (EtOH, c=1), and the R,S-diastereomer of the title compound, m.p. 153°–156°, $[\alpha]_D{}^{26} = +9.7°$ (EtOH, c=1).

In a similar manner to that described in Example 13, Step 1, substitute the appropriate acetylthio compounds and amides and separate by chromatography to obtain:

N-(3-Acetylthio-2-benzylpropionyl)-S-(4-methylbenzyl)-L-cysteine amide, Isomer A, $[\alpha]_D{}^{26} = -38.2°$ (MeOH);

N-(3-Acetylthio-2-benzylpropionyl)-S-(4-methylbenzyl)-L-cysteine amide, Isomer B, $[\alpha]_D{}^{26} = -1.6°$ (MeOH);

N-[3-Acetylthio-2-(4-chlorobenzylpropionyl)]-L-methionine amide, Isomer A;

N-[3-Acetylthio-2-(4-chlorobenzylpropionyl)]-L-methionine amide, Isomer B, m.p. 166°–169°;

N-(3-Acetylthio-2(S)-phenylpropionyl)-S-3-(2-thienyl)alanine amide, a white solid, TLC $R_f = 0.35$ (1% EtOH/EtOAc); and N-(3-Acetylthio-2(R)-phenylpropionyl)-S-3-(2-thienyl)alanine amide, TLC $R_f = 0.30$ (1% EtOH/EtOAc).

Treat the amides obtained above in a manner similar to that described in Example 13, Step 2 to obtain:

N-[2-(4-Chlorobenzyl)-3-mercaptopropionyl]-L-methionine amide, Isomer A, m.p. 194°, $[\alpha]_D{}^{26} = +1.2°$ (MeOH);

N-[2-(4-Chlorobenzyl)-3-mercaptopropionyl]-L-methionine amide, Isomer B, $[\alpha]_D{}^{26} = -65.2°$ (MeOH);

N-(2-Benzyl-3-mercaptopropionyl)-S-(4-methylbenzyl)-L-cysteine amide, Isomer A, m.p. 130°-2°, $[\alpha]_D{}^{26} = -4.2°$ (MeOH);

N-(2-Benzyl-3-mercaptopropionyl)-S-(4-methylbenzyl)-L-cysteine amide, Isomer B, $[\alpha]_D{}^{26} = -29.0°$ (MeOH);

N-(2(S)-Benzyl-3-mercaptopropionyl)-S-3-(2-thienyl)alanine amide, a white solid, TLC $R_f = 0.40$ (4% MeOH/CH2Cl2); and N-(2(R)-Benzyl-3-mercaptopropionyl)-S-3-(2-thienyl)alanine amide, TLC $R_f = 0.35$ (4% MeOH/CH2Cl2).

EXAMPLE 14

N-(3-Benzoylthio-2-Benzylpropionyl)-L-Methionine Amide

Prepare the R and S enantiomers of 3-benzoylthio-2-benzylpropionic acid according to the procedure described in U.S. Pat. No. 4,329,495, herein incorporated by reference.

In a manner similar to that described in Example 1, Step 1, condense each acid separately with L-methionine amide to obtain
N-(3(S)-benzoylthio-2-benzylpropionyl)-L-methionine amide, m.p. 178°–180°, $[\alpha]_D^{26} = -97.6°$ (MeOH); and
N-(3(R)-benzoylthio-2-benzylpropionyl)-L-methionine amide, m.p. 145°–149°, $[\alpha]_D^{26} = +32.9°$ (CHCl$_3$).

EXAMPLE 15

N-[2-Benzyl-3-Mercaptopropionyl]-L-Aspartic Acid β-Benzyl Ester

In similar fashion to that described in Example 12, Step 2, convert L-aspartic acid β-benzyl ester to N-(3-acetylthio-2-benzylpropionyl)-L-aspartic acid, β-benzyl ester.

Treat with NH$_3$/MeOH as in Example 12, Step 3 to give the title compound, $[\alpha]_D^{26} = -5.7°$ (EtOH, c=0.5).

EXAMPLE 16

N-[N-(2-Benzyl-3-Mercaptopropionyl)-L-Phenyalanyl]-L-Alanine

Using the procedure of Example 1, L-phenylalanyl-L-alanine benzyl ester hydrochloride to N-(3-acetylthio-2-benzylpropionyl)-L-phenylalanyl]-L-alanine, benzyl ester.

Treat with NaOH as in Example 1, Step 2 to give the crude title compound. React the product (0.62 g) with zinc powder (0.5 g) and 5N HCl (10 ml) in 20 ml MeOH for 1 hour Concentrate the mixture, extract with CH$_2$Cl$_2$, dry, and remove the solvent to give the title compound, $[\alpha]_D^{26} = -23.1°$ (EtOH, c=0.5).

Use the same procedure to prepare N-(N-(2-benzyl-3-mercaptopropionyl)-L-phenylalanyl-L-leucine, $[\alpha]_D^{26} = -20.8°$ (EtOH, c=0.5).

EXAMPLE 17

N-[N-(2-Benzyl-3-Mercaptopropionyl)-L-alanyl]-L-Proline

Step 1: N-[N-(3-Acetylthio-2-Benzylpropionyl)-L-Alanyl]-L-Proline: Using the procedure of Example 12, Step 2, convert L-alanyl-L-proline to N-[N-(3-acetylthio-2-benzylpropionyl)-L-alanyl]-L-proline, a white foam, $[\alpha]_D^{26} = -81.8°$ (MeOH).

Step 2: N-[N-(2-Benzyl-3-Mercaptopropionyl)-L-Alanyl]-L-Proline: Treat the product from Step 1 with methanol saturated with ammonia as described in Example 12, Step 3 (before chromatography). Treat the resultant residue with zinc powder as described in Example 17. Chromatograph the product on flash grade silica gel using CH$_2$Cl$_2$:MeOH:NH$_4$OH (97.5:2.5:0.25) to give the title compound, $[\alpha]_D^{26} = -118.2°$ (MeOH).

EXAMPLE 18

N-(2(R,S)-Acetylthiomethyl-3-Phenylpropionyl)-S-Methionine Piperidine Amide

Step 1: Combine N-(t-butoxycarbonyl)-S-methionine (1.50 g, 6.0 mmol), piperidine (0.51 g, 6.0 mmol) and HOBT (0.91 g, 6.0 mmol) in DMF (40 ml). Add DEC (1.15 g, 6.0 mmol). Stir 5 hours, concentrate in vacuo, and partition between EtOAc and H$_2$O. Wash with aqueous NaHCO$_3$, dry, and concentrate to obtain the piperidine amide as a colorless oil (TLC single spot R$_f$=0.6 in 5% MeOH/CH$_2$Cl$_2$).

Step 2: Treat the amide of Step 1 with 6M HCl/dioxane (25 ml). After 0.5 hr., concentrate in vacuo to obtain the amine hydrochloride as a foam.

Step 3: Treat the above amide hydrochloride of Step 2 with triethylamine (1.35 g, 15 mmol) in CH$_3$CN:H$_2$O 2:1 (60 ml). Add 2-acetylthiomethyl-3-phenylpropionyl chloride (1.37 g, 5.4 mmol), stir 1 hr., add 1N HCL (15 ml), and extract with EtOAc. Dry and concentrate to obtain a brown oil. Chromatograph on silica gel (2% MeOH/CH$_2$Cl$_2$ and R,S-diastereomers, as a yellow oil, $[\alpha]_D^{26} = -31.7°$ (EtOH, c=1).

Using a similar procedure, prepare the following mixtures of diastereomers:

N-(2(R,S)-acetylthiomethyl-3-phenylpropionyl)-S-methionine 4-methylbenzyl amide, a 1:1 mixture of diastereomers, a colorless foam, $[\alpha]_D^{26} = -18.6°$ (EtOH, c=1);

N-(2(R,S)-acetylthiomethyl-3-phenylpropionyl)-S-methionine 2-hydroxyethyl amide, a 3:2 mixture of the S,S- and R,S-diastereomers, $[\alpha]_D^{26} = -31.1°$ (EtOH, c=1); and N-(2(R,S)-acetylthiomethyl-3-phenylpropionyl)-S-methionine morpholine amide, a 1:1 mixture of diastereomers, a yellow oil, $[\alpha]_D^{26} = -30.0°$ (EtOH, c=1).

Using a similar procedure, prepare N-(2(R,S)-acetylthiomethyl-3-phenylpropionyl)-S-methionine pyrrolidine amide. Chromatograph on silica gel (elute with diethylether) to obtain the S,S-diastereomer as a yellow solid, $[\alpha]_D^{26} = -49.4°$ (EtOH, c=1) and the R,S-diastereomer as a white solid, $[\alpha]_D^{26} = -6.1°$ (EtOH, c=1).

Again, using a procedure similar to Example 18, prepare N-(2(S)-acetylthiomethyl-3-phenylpropionyl)-S-methionine 2-dimethylaminoethyl amide, a beige solid, $[\alpha]_D^{26} = -58.3°$ (EtOH, c=1). Dissolve in CH$_2$Cl$_2$, add HCl/Et$_2$O and concentrate to obtain the hydrochloride salt as a yellow gum.

EXAMPLE 19

N-(2(S)-Acetylthiomethyl-3-Phenylpropionyl)-S-Methionine 2-(2-Chloroethoxy)Ethyl Ester Step 1: Combine N-(t-butoxycarbonyl)-S-methionine (2.0 g, 8.0 mmol), 2-(2-chloroethoxy)ethanol (0.99 g, 8.0 mmol) and 4-dimethylaminopyridine in CH$_2$Cl$_2$ (35 ml). Add DEC (1.54 g, 8.0 mmol). Stir 1 hour, concentrate, and partition between Et$_2$O and 1N HCl. Dry and concentrate to obtain the ester as an oil.

Step 2: Treat the ester of Step 1 with 6M HCl/dioxane (25 ml). After 35 min., concentrate and triturate the residue with Et$_2$O to obtain the amine hydrochoride as a solid.

Step 3: Treat the hydrochloride of Step 2 (1.30 g, 4.5 mmol) with triethylamine (0.90 g, 8.9 mmol) in CH$_3$CN:H$_2$O 2:1 (60 ml). Add 2-acetylthiomethyl-3-phenylpropionyl chloride (1.14 g, 4.5 mmol), stir 1 hour, add 1N HCl (13 ml), and extract with EtOAc. Dry and concentrate. Chromatograph on silica gel (Et$_2$O/hexane 6:4 as eluent) to obtain the title compound as a yellow solid, m.p. 58°–63°, $[\alpha]_D^{26} = -44.7°$ (EtOH, c=1).

In a similar manner, prepare mixtures of esters and separate by chromatography to obtain:

N-(2(S)-acetylthiomethyl-3-(4-methyphenyl)propionyl)-S-methionine 2-(2-chloroethoxy)ethyl ester, a yellow solid, $[\alpha]_D^{26} = -47.7°$ (EtOH, c=1);

N-(2(R)-acetylthiomethyl-3-(4-methyphenyl)propionyl)-S-methionine 2-(2-chloroethoxy)ethyl ester, a yellow solid, $[\alpha]_D^{26} = -2.5°$ (EtOH, c=1);

N-(2(S)-acetylthiomethyl-3-(2-methylphenyl)propionyl)-S-methionine 2-(2-chloroethoxy) ethyl ester, a yellow solid, $[\alpha]_D^{26} = -46.4°$ (EtOH, c=1); and N-(2(R)-acetylthiomethyl-3-(2-methylphenyl)propionyl)-S-methionine 2-(2-chloroethoxy) ethyl ester, a yellow solid, $[\alpha]_D^{26} = -17.7°$ (EtOH, c=1).

EXAMPLE 20

N-(2(R,S)-Acetylthiomethyl-3-Phenylpropionyl)-S-Methionine Diethylaminocarbonylmethyl Ester Step 1: Combine N-(t-butoxycarbonyl)-S-methionine (1.50 g, 6.0 mmol), N,N-diethylbromoacetamide (1.16 g, 6.0 mmol) and Cs$_2$CO$_3$ (0.97 g, 3.0 mmol) in DMF (40 ml), stir 18 hours, and partition between EtOAc and H$_2$O. Wash with 1N NaCHO$_3$, dry and concentrate to obtain the ester as an oil.

Step 2: Treat the ester as in Example 19, Steps 2 and 3, to obtain the title compound as a 3:2 mixture of S,S- and R,S-diastereomers, yellow oil, $[\alpha]_D^{26} = -30.4°$ (EtOH, c=1).

EXAMPLE 21

N-(2(S)-Benzoylthiomethyl-3-Phenylpropionyl)-S-Methionine 2-(2-Chloroethoxy)Ethyl Ester Combine the product of Example 19, Step 2 (1.00 g, 3.4 mmol) with 2(S)-benzoylthiomethyl-3-phenylpropionic acid (see U.S. Pat. No. 4,329,495) (1.03 g, 3.4 mmol), HOBT (0.52 g, 3.4 mmol) and triethylamine (0.86 g, 8.6 mmol) in DMF (35 ml). Add DEC (0.65 g, 3.4 mmol) and stir 18 hours. Concentrate and partition between EtOAc and H$_2$O. Wash with 1N NaHCO$_3$, dry and concentrate. Chromatograph the resultant oil on silica gel (Et$_2$O:hexane 3:1 as eluant) to obtain the title compound, a white solid, $[\alpha_D^{26} = -50.6°$ (EtOH, c=1).

The R,S-diastereomer of the title compound may be prepared in a similar manner.

In a similar manner, prepare the following esters of N-(2(S)-benzoylthiomethyl-3-phenylpropionyl)-S-methionine:

2-(ethoxy)ethyl ester, a yellow solid, $[\alpha]_D^{26} = -49.9°$ (EtOH, c=1);

2-(2-methoxyethoxy)ethyl ester, a white solid, $[\alpha]_D^{26} = -48.9°$ (EtOH, c=1);

2,2-dimethyl-1,3-dioxolan-4-yl or methyl ester, a white solid, m.p. 76°-8°, $[\alpha]_D^{26} = -58.6°$ (MeOH, c=1).

The last compound may be converted to the 2,3-dihydroxypropyl ester by hydrolysis with AGW-50 resin (H+ form) in CH$_3$CN:H$_2$O 2:1 for 20 hours and subsequent silica gel chromatography. The product ester is a white solid, $[\alpha]_D^{26} = -57.4°$ (MeOH, c=1).

EXAMPLE 22

N-(3-Phenyl-2(S)-(4-Pyridylcarbonylthiomethyl)Propionyl)-S-Methionine Amide and
N-(3-Phenyl-2(R)-(4-Pyridylcarbonylthiomethyl)Propionyl)-S-Methionine Amide To N-2(R,S)-mercaptomethyl-3-phenylpropionyl)-S-methionine amide (0.32 g, 1.0 mmol) and triethylamine (0.19 g, 1.9 mmol) in CH$_2$Cl$_2$ (30 ml), add isonicotinoyl chloride hydrochloride (0.19 g, 1.1 mmol). After 3 hours, concentrate and chromatograph on silica (6% MeOH/CH$_2$Cl$_2$ as eluent) to obtain:

the S,S-diastereomer, a yellow solid, m.p. 157°-160°, $[\alpha]_D^{26} = -68.3°$ (EtOH, c=1); and
the S,R-diastereomer, a white solid, $[\alpha]_D^{26} = +27.6°$ (EtOH, c=1).

EXAMPLE 23

N-(2(R,S)-Mercaptomethyl-3-Phenylpropionyl)-S-Tryptophan 4-Methylpiperazine Amide Hydrochloride
and
N-(2(R,S)-Mercaptomethyl-3-Phenylpropionyl)-S-Tryptophan 2-(4-Pyridyl)Ethyl Amide Hydrochloride Step 1: Using the procedure of Example 18, prepare N-(2(R,S)-acetythiomethyl-3-phenylpropionyl)-S-tryptophan 4-methylpiperazine amide and convert to the hydrochloride, a brown foam, mass spectrum M+ =506.

Similarly, prepare the hydrochloride of the 2-(4-pyridyl)ethyl amide, an off-white foam, mass spectrum M+ =528.

Step 2: Using the procedure of Example 12, Step 3, convert the products of Step 1 to the title compounds: the 4-methylpiperazine amide hydrochloride, an off-white foam, mass spectrum M+ =486; and
the 2-(4-pyridyl)ethyl amide hydrochloride, a beige foam, mass spectrum M+ =464.

EXAMPLE 24

N-(2-Benzoylthiomethyl-3-Phenylpropionyl)-Methionine 4-Methylpiperazine Amide Hydrochloride
(S,S-and R,S-diastereomers)

Using procedures similar to Example 18, Step 1 and Example 1, Step 1, prepare the S,S-diastereomer of the title compound, a white solid, m.p. 157°-158°. Similarly, prepare the R,S diastereomer, a white solid, 114°-116°.

In a similar manner prepare the diastereomeric mixture N-[(2(R,S)-benzoylthiomethyl-3-phenylpropionyl]-S-methionine 2-(4-pyridyl)ethyl amide, a white solid, m.p. 108°-110°.

EXAMPLE 25

N-(2(S)-Benzoylthiomethyl-3-Phenylpropionyl)-S-methionine S-sulfoxide2-(2-Chloroethoxy)Ethyl Ester To the title compound of Example 21 (1.00 g, 1.86 mmol) in MeOH (25 ml) add 30% H$_2$O$_2$ (0.22 g, 4 mmol), stir 45 min. and concentrate. Triturate the residue with Et$_2$O:hexane 3:1 to obtain the title compound, a white solid, as a 1:1 mixture of sulfoxide diastereomers, NMR (CDCl$_3$) δ2.42, 2.45.

In a similar manner, prepare the sulfoxide of the R,S-diastereomer of the title compound, a colorless oil, $[\alpha]_D^{26} = -2.8°$ (EtOH, c=1).

Also in a similar manner prepare the sulfoxide of N-(2(S)-acetythiomethyl-3-phenylpropionyl)-S-methionine amide, a beige solid, $[\alpha]_D^{26} = -50.6°$ (EtOH, c=1).

EXAMPLE 26

N-(2(S)-Mercaptomethyl-3-Phenylpropionyl)-S-Methionine Sulfoxide

Treat the title compound of Example 25 (the S,S-diastereomer) (0.46 g, 1.0 mmol) with MeOH (8 ml) and 1N NaOH (4 ml). Stir 18 hr. under N$_2$, concentrate and add 1N HCl (4 ml). Extract with EtOAc, dry, concentrate and chromatograph on silica (CH$_2$Cl$_2$:MeOH:HOAc 90:9:1 as eluent) to obtain the title compound as a white solid, NMR (DMSO) δ2.45, 2.46.

We claim:

1. A method of treating hypertension or congestive heart failure comprising administering to a hypertensive mammal an antihypertensive effective amount of a combination of an atrial natriuretic factor and a mercaptoacylamino acid compound having the structural formula

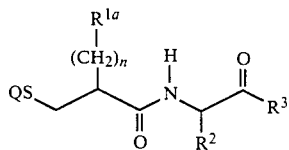

wherein
$R^{1a}$ is $Y-C_6H_4-$, $Y-C_6H_4S-$, $Y-C_6H_4O-$,

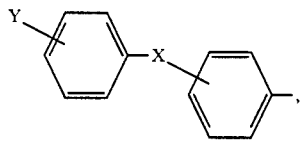

α-naphthyl, β-naphthyl, furyl, thienyl, benzofuryl, benzothienyl, $H_2N(CH_2)_m-$, diphenylmethyl,

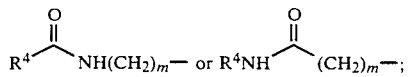

$R^2$ is alkyl, alkyl-S(O)$_{0-2}$(CH$_2$)$_q-$, $R^{14}$(CH$_2$)$_k$S(O)$_{0-2}$(CH$_2$)$_q-$, alkyl-O(CH$_2$)$_q-$, $R^5$(CH$_2$)$_k-$O(CH$_2$)$_q-$, $R^5$(CH$_2$)$_q-$, $N_2N(CH_2)_q-$, cycloalkyl(CH$_2$)$_k-$, $R^{13}$CONH(CH$_2$)$_q-$, $R^{13}$NHCO(CH$_2$)$_q-$ or $R^6$OCO(CH$_2$)$_q-$;
$R^3$ is $-OR^7$, $-NR^7R^8$,

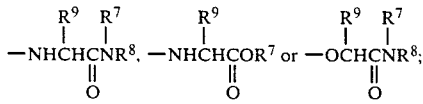

$R^4$ and $R^{13}$ are independently hydrogen, alkyl or $Y^1-C_6H_4-$;
$R^5$ is $Y^2-C_6H_4-$, $Y^2-C_6H_4S-$, $Y^2-C_6H_4O-$, α-naphthyl, β-naphthyl, furyl, thienyl, benzofuryl, benzothienyl, indolyl or

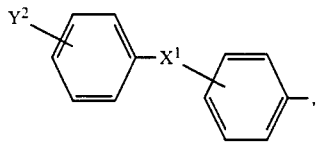

provided that when $R^5$ is $Y^2-C_6H_4S-$ or $Y^2C_6H_4O-$, k is 2 or 3;
$R^{14}$ is $R^{5,}$ mono-unsaturated lower alkyl, hydroxy, alkoxy or alkylthio, provided that when $R^{14}$ is hydroxy or alkoxy, k is 2 or 3 and when $R^{14}$ is mono-unsaturated alkyl or alkylthio, k is 1, 2 or 3;
$R^{6,}$ $R^7$ and $R^8$ are independently H, alkyl, hydroxyalkyl, dihydroxyalkyl, alkoxyalkyl, dialkoxyalkyl, alkoxyalkoxyalkyl, haloalkyl, (haloalkoxy)alkyl, aminoalkyl, alkylaminoalkyl, dialkylaminoalkyl, arylalkyl or alkyl substituted with a 5-6 membered saturated ring comprising 1-2 oxygen atoms as ring members wherein the ring carbon atoms may be substituted with 0-2 alkyl substituents, or $R^7$ and $R^8$ together with the nitrogen to which they are attached complete a 5-7 membered ring, wherein one of the 4-6 ring members containing $R^7$ and $R^8$ may be a nitrogen atom, an alkyl-substituted nitrogen atom or an oxygen atom, and wherein the ring may be substituted on the ring carbon atoms with substituents chosen from alkyl and hydroxy groups;
$R^9$ is hydrogen, alkyl, carboxyalkyl, mercaptoalkyl, alkylthioalkyl, aminoalkyl, hydroxyalkyl, phenylalkyl, hydroxyphenylalkyl, guanidinoalkyl, imidazolylalkyl, indolylalkyl, or carbamoylalkyl;
n is 0-2;
m and k are independently 0-3;
q is 1-4;
X and $X^1$ are independently a bond, $-O-$, $-S-$, or $-CH_2-$;
Q is hydrogen or $R^{10}CO-$;
$R^{10}$ is alkyl, hydroxyalkyl, alkoxyalkyl, alkylaminoalkyl, dialkylaminoalkyl, $Y^3-C_6H_4$-alkyl, alkoxy, $Y^3-C_6H_4-$, naphthyl, furyl, thienyl or pyridyl;
Y, $Y^1$, $Y^2$ and $Y^3$ independently represent one or more substituents selected from H, alkyl, cycloalkyl, alkoxy, OH, F, Cl, Br, CN, $-CH_2NH_2$, $-CO_2H$, $-CO_2$alkyl, $-CONH_2$ and phenyl;
or a pharmaceutically acceptable addition salt thereof.

2. A method of claim 1 wherein the mercaptoacylamino acid is selected from the (S,S) and (R,S) isomers of:

N-[3-phenyl-2-mercaptomethylpropionyl]-S-methionine;

N-[3-phenyl-2-mercaptomethylpropionyl]-S-methionine amide;

N-(2-benzoylthiomethyl-3-phenylpropionyl)-S-methionine 2-(2-chloroethoxy)ethyl ester;

N-(2-benzoylthiomethyl-3-phenylpropionyl)-S-methionine 2-(ethoxy)ethyl ester;

N-(2-benzoylthiomethyl-3-phenylpropionyl)-S-methionine 2,2-dimethyl-1,3-dioxolane-4-methyl ester;

N-(2-benzoylthiomethyl-3-phenylpropionyl)-S-methionine 2-(2-methoxyethoxy)ethyl ester;

N-(2-acetylthiomethyl-3-phenylpropionyl)-S-methionine 2-(2-chloroethoxy)ethyl ester;

N-(2-acetylthiomethyl-3-(4-methylphenyl)propionyl)-S-methionine 2-(2-chloroethoxy)ethyl ester;

N-2(acetylthiomethyl-3-(2-methylphenyl)propionyl)-S-methionine 2-(2-chloroethoxy)ethyl ester;

N-(2-benzoylthiomethyl-3-phenylpropionyl)-S-methionine 2,3-dihydroxypropyl ester; and N-(2-benzoylthiomethyl-3-phenylpropionyl)-S-methionine sulfoxide 2-(2-chloroethoxy)ethyl ester.

3. A method of claim 1 wherein the atrial natriuretic factor is chosen from α human AP 21, α human AP 28, α human AP 23, α human AP 24, α human AP 25, α human AP 26, α human AP 33, and the corresponding atrial natriuretic factor wherein the methionine at position 12 is replaced by isoleucine.

4. A method of claim 3 wherein the mercaptoacylamino acid is selected from the (S,S) and (R,S) isomers of:

N-[3-phenyl-2-mercaptomethylpropionyl]-S-methionine;

N-[3-phenyl-2-mercaptomethylpropionyl]-S-methionine amide;

N-(2-benzoylthiomethyl-3-phenylpropionyl)-S-methionine 2-(2-chloroethoxy)ethyl ester;

N-(2-benzoylthiomethyl-3-phenylpropionyl)-S-methionine 2-(ethoxy)ethyl ester;

N-(2-benzoylthiomethyl-3-phenylpropionyl)-S-methionine 2,2-dimethyl-1,3-dioxolan-4-methyl ester;

N-(2-benzoylthiomethyl-3-phenylpropionyl)-S-methionine 2-(2-methoxyethoxy)ethyl ester;

N-(2-acetylthiomethyl-3-phenylpropionyl)-S-methionine 2-(2-chloroethoxy)ethyl ester;

N-(2-acetylthiomethyl-3-(4-methylphenyl)propionyl)-S-methionine 2-(2-chloroethoxy)ethyl ester;

N-2(-acetylthiomethyl-3-(2-methylphenyl)propionyl)-S-methionine 2-(2-chloroethoxy)ethyl ester;

N-(2-benzoylthiomethyl-3-phenylpropionyl)-S-methionine 2,3-dihydroxypropyl ester; and N-(2-benzoylthiomethyl-3-phenylpropionyl)-S-methionine sulfoxide 2-(2-chloroethoxy)ethyl ester.

* * * * *

UNITED STATES PATENT AND TRADEMARK OFFICE
CERTIFICATE OF CORRECTION

PATENT NO. : 5,061,710

DATED : October 29, 1991

INVENTOR(S) : Haslanger, et al

It is certified that error appears in the above-identified patent and that said Letters Patent is hereby corrected as shown below:

On the title page, delete the list of inventors (section [75]) and insert instead:

-- Martin F. Haslanger, Ridgewood, N.J.;
Bernard R. Neustadt, West Orange, N.J.;
Elizabeth M. Smith, Verona, N.J.;
Michael F. Czarniecki, Watchung, N.J.; and
Laura S. Lehman de Gaeta, La Jolla, Calif. --

Signed and Sealed this

Thirtieth Day of March, 1993

Attest:

STEPHEN G. KUNIN

*Attesting Officer*

*Acting Commissioner of Patents and Trademarks*